(12) United States Patent
Borneman et al.

(10) Patent No.: US 10,197,641 B2
(45) Date of Patent: Feb. 5, 2019

(54) USING A CAVITY TO POLARIZE A SPIN ENSEMBLE

(71) Applicant: QUANTUM VALLEY INVESTMENT FUND LP, Waterloo (CA)

(72) Inventors: Troy Borneman, Waterloo (CA); David G. Cory, Branchton (CA); Christopher James Wood, Waterloo (CA)

(73) Assignee: Quantum Valley Investment Fund LP, Waterloo (CA)

( * ) Notice: Subject to any disclaimer, the term of this patent is extended or adjusted under 35 U.S.C. 154(b) by 590 days.

(21) Appl. No.: 14/787,575

(22) PCT Filed: Jan. 31, 2014

(86) PCT No.: PCT/CA2014/000065
§ 371 (c)(1),
(2) Date: Oct. 28, 2015

(87) PCT Pub. No.: WO2014/176662
PCT Pub. Date: Nov. 6, 2014

(65) Prior Publication Data
US 2016/0109540 A1    Apr. 21, 2016

Related U.S. Application Data

(60) Provisional application No. 61/819,103, filed on May 3, 2013.

(51) Int. Cl.
*G01R 33/28* (2006.01)
*G01N 24/08* (2006.01)
(Continued)

(52) U.S. Cl.
CPC ........... *G01R 33/282* (2013.01); *G01N 24/08* (2013.01); *G01N 24/10* (2013.01); *G01R 33/30* (2013.01);
(Continued)

(58) Field of Classification Search
CPC ..... G01R 33/282; G01N 247/08; G01N 24/08
(Continued)

(56) References Cited

U.S. PATENT DOCUMENTS

| 4,825,162 A | 4/1989 | Roemer et al. |
| 4,947,121 A | 8/1990 | Hayes |

(Continued)

FOREIGN PATENT DOCUMENTS

| CA | 2643306 | 11/2007 |
| DE | 102012202416 | 6/2013 |

(Continued)

OTHER PUBLICATIONS

Abe, E. et al., "Electron spin ensemble strongly coupled to a three-dimensional microwave cavity," Applied Physics Letters 98, 251108, Jun. 21, 2011, pp. 1-3; American Institute of Physics; AIP Publishing; Melville, NY; US.

(Continued)

*Primary Examiner* — Reena Aurora
(74) *Attorney, Agent, or Firm* — Henry Patent Law Firm PLLC

(57) ABSTRACT

In some aspects, polarization of a spin ensemble can be increased using cavity-based techniques. A resonator applies drive field to a spin ensemble in a static magnetic field. The drive field couples the spin ensemble with a cavity, and the coupling increases the polarization of the spin ensemble. In some cases, the cavity is detuned from the spin-resonance frequency, and the Rabi frequency associated with the drive field can be matched to the cavity detuning.

18 Claims, 8 Drawing Sheets

(51) Int. Cl.
| | |
|---|---|
| G01R 33/30 | (2006.01) |
| G01R 33/38 | (2006.01) |
| G01R 33/44 | (2006.01) |
| G01R 33/385 | (2006.01) |
| G01R 33/50 | (2006.01) |
| G01R 33/56 | (2006.01) |
| G01N 24/10 | (2006.01) |
| G01R 33/60 | (2006.01) |

(52) U.S. Cl.
CPC ..... *G01R 33/3804* (2013.01); *G01R 33/3856* (2013.01); *G01R 33/44* (2013.01); *G01R 33/50* (2013.01); *G01R 33/56* (2013.01); *G01R 33/60* (2013.01)

(58) Field of Classification Search
USPC .......................................................... 324/309
See application file for complete search history.

(56) References Cited

U.S. PATENT DOCUMENTS

| | | | |
|---|---|---|---|
| 5,030,914 | A | 7/1991 | Jasper |
| 5,154,603 | A | 10/1992 | Sepponen |
| 5,258,710 | A | 11/1993 | Black et al. |
| 6,437,570 | B2 | 8/2002 | Marek |
| 6,441,617 | B2 | 8/2002 | Marek |
| 6,472,870 | B1 | 10/2002 | Bendall et al. |
| 6,677,751 | B1 | 1/2004 | Marek |
| 6,812,705 | B1 | 11/2004 | Sellers |
| 7,205,764 | B1 | 4/2007 | Anderson et al. |
| 7,403,008 | B2 | 7/2008 | Blank et al. |
| 7,474,099 | B2 | 1/2009 | Boesel et al. |
| 7,639,007 | B2 | 12/2009 | Hutton et al. |
| 7,646,200 | B2 | 1/2010 | Slade et al. |
| 7,701,218 | B2 | 4/2010 | Noonan et al. |
| 7,710,114 | B2 | 5/2010 | Hattori et al. |
| 8,703,201 | B2 | 4/2014 | Belzer et al. |
| 2001/0013779 | A1 | 8/2001 | Marek |
| 2003/0006852 | A1 | 1/2003 | Weitekamp |
| 2007/0063700 | A1 | 3/2007 | Levitt et al. |
| 2008/0204014 | A1 | 8/2008 | Desvaux et al. |
| 2009/0085562 | A1 | 4/2009 | Strange et al. |
| 2009/0121712 | A1 | 5/2009 | Han et al. |
| 2009/0134868 | A1 | 5/2009 | Noonan |
| 2011/0150779 | A1 | 6/2011 | Han et al. |
| 2012/0114851 | A1 | 5/2012 | Kalechofsky et al. |
| 2016/0061915 | A1 | 3/2016 | Teklemariam et al. |
| 2016/0069966 | A1 | 3/2016 | Borneman et al. |
| 2016/0077177 | A1 | 3/2016 | Teklemariam et al. |
| 2016/0109540 | A1 | 4/2016 | Borneman et al. |

FOREIGN PATENT DOCUMENTS

| | | |
|---|---|---|
| JP | 5-2060 | 1/1993 |
| JP | 10293167 | 11/1998 |
| JP | 2001153938 | 6/2001 |
| JP | 2001242230 | 9/2001 |
| JP | 2005114682 | 4/2005 |
| JP | 2005199047 | 7/2005 |
| JP | 2006066603 | 3/2006 |
| JP | 2007064984 | 3/2007 |
| JP | 2007-538244 | 12/2007 |
| JP | 2008528991 A | 7/2008 |
| JP | 2008534976 | 8/2008 |
| JP | 2009501329 | 1/2009 |
| JP | 2009053199 | 3/2009 |
| JP | 2009527768 | 7/2009 |
| WO | 97/37239 | 10/1997 |
| WO | 2005/114244 | 12/2005 |
| WO | 2010112137 | 1/2010 |

OTHER PUBLICATIONS

Abragam, A, "The Principles of Nuclear Magnetism," Oxford University Press; pp. 22-27, 364-378, 401-409; 1961; London, UK.

Agarwal, G.S., "Quantum Optics," Springer-Verlag, Berlin, 1974, pp. 200-208; Cambridge University Press; Cambridge, UK.

Allison, G. et al., "A superconducting resonator designed for coupling to spin based qubits in quantum dots", Journal of Physics: Conference Series 245, 012024, 2010, pp. 1-4; IOP Publishing; Bristol, UK.

Bachar et al., "Nonlinear Induction Detection of Electron Spin Resonance," Applied Physics Letters 101, 022602, Jul. 12, 2012, pp. 1-4; AIP Publishing; Melville, NY; US.

Belthangady, C. et al., "Dressed-State Resonant Coupling between Bright and Dark Spins in Diamond," Physical Review Letters 110, 157601, Apr. 12, 2013, pp. 1-5; The American Physical Society, Ridge, NY; US.

Benningshof et al., "Superconducting Microstrip Resonator for Pulsed ESR of Thin Films," Journal of Magnetic Resonance 230, Feb. 5, 2013, pp. 84-87; Elsevier; Amsterdam, NL.

Bloembergen, et al, "Nuclear Magnetic Resonance in the Cesium Halides," Physical Review, vol. 110, No. 4, May 15, 1958, pp. 865-876; The American Physical Society, Ridge, NY; US.

Boero, G. et al. "Room temperature strong coupling between a microwave oscillator and an ensemble of electron spins", Journam of Magnetic Resonance 231, Apr. 18, 2013, pp. 133-140; Elsevier; Amsterdam, NL.

Bonifacio, et al, "Coherent Spontaneous Emission," Physical Review A, vol. 2, No. 2, Aug. 1970, pp. 336-347; The American Physical Society; Ridge, NY; US.

Borneman et al., "Application of Optimal Control to CPMG Refocusing Pulse Design," Journal of Magnetic Resonance 207, Sep. 15, 2010, pp. 220-233; Elsevier; Amsterdam, NL.

Borneman, et al., "Bandwidth-limited Control and Ringdown Suppression in High-Q Resonators," Journal of Magnetic Resonance 225, Oct. 31, 2012, pp. 120-129; Elsevier, Amsterdam, NL.

Borneman, T.W. et al., "Parallel Information Transfer in a Multinode Quantum Information Processor," Physical Review Letters 108, 140502, Apr. 6, 2012, pp. 1-5; American Physical Society; Ridge, NY; US.

Brahms et al; "Cavity-aided magnetic resonance microscopy of atomic transport in optical lattices", Nature Physics, 2011; 7(8):604-607; Nature Publishing Group; Macmillan Publishers Limited; London, UK.

Brahms et al; "Spin optodynmics analog of cavity optomechanics"; Physical Review A 82; pp. 041804-1 to 041804-4; (2010); Oct. 29, 2010; The American Physical Society; Ridge, NY; US.

Breuer et al, "The Theory of Open Quantum Systems," Oxford University Press USA, 2002, pp. 441-451; Oxford University Press USA; New York; US.

Bullough, R.K., "Photon, Quantum and Collective, Effects from Rydberg Atoms in Cavities," Hyperfine Interactions 37, 1987, pp. 71-108; J.C. Baltzer A.G. Scientific Publishing Company; Amsterdam, NL.

Canadian International Searching Authority; International Search Report and Written Opinion issued in International Application No. PCT/CA2014/000065 dated Apr. 29, 2014; 7 pages; Gatineau, Quebec, CA.

Canadian International Searching Authority; International Search Report and Written Opinion issued in International App. No. PCT/CA2014/000070; 9 pages; dated Apr. 30, 2014; Gatineau, Quebec, CA.

Canadian International Searching Authority; International Search Report and Written Opinion issued in International Application No. PCT/CA2014/000390 dated Jul. 24, 2014; 9 pages; Gatineau, Quebec, CA.

Canadian International Searching Authority; International Search Report and Written Opinion issued in International Application No. PCT/CA2014/000069; 11 pages; dated Apr. 30, 2014; Gatineau, Quebec, CA.

Canadian International Searching Authority; International Search Report and Written Opinion issued in International Application No. PCT/CA2014/000066 dated May 1, 2014; 11 pages; Gatineau, Quebec, CA.

(56) References Cited

OTHER PUBLICATIONS

Cappellaro, P. et al., "Coherence and Control of Quantum Registers Based on Electronic Spin in a Nuclear Spin Bath," Physical Review Letters 102, 210502, May 29, 2009, pp. 1-4; The American Physical Society; Ridge, NY; US.
Chiorescu, I. et al., "Magnetic strong coupling in a spin-photon system and transition to classical regime," Physical Review B 82, 024413, Jul. 14, 2010, pp. 1-7; The American Physical Society, Ridge, NY; US.
Deutsch, I.H. et al., "Quantum control and measurement of atomic spins in polarization spectroscopy," Center for Quantum Information and Control, Sep. 24, 2009, pp. 1-42; The University of New Mexico; Albuquerque, NM; US.
Dicke, R.H., "Coherence in Spontaneous Radiation Processes," Physical Review, vol. 93, No. 1, Jan. 1, 1954, pp. 99-110; The American Physical Society; Ridge, NY; US.
Eaton et al., "A signal-to-noise Standard for Pulsed EPR," Journal of Magnetic Resonance 205, Apr. 24, 2010, pp. 109-113; Elsevier; Amsterdam, NL.
Engelke, F., "Virtual Photons in Magnetic Resonance," Concepts in Magnetic Resonance Part A, vol. 36A(5), Jul. 29, 2010, pp. 266-339; Wiley Online Library; Wiley Periodicals, Inc.; Hoboken, NJ; US.
Garraway, B.M., "The Dicke model in quantum optics: Dicke model revisited," Philosophical Transactions of the Royal Society A 369, Feb. 14, 2011, pp. 1137-1155; Royal Society Publishing; London, UK.
Geerlings, K. et al., "Demonstrating a Driven Reset Protocol for a Superconducting Qubit," Physical Review Letters 110, 120501, Mar. 22, 2013, pp. 1-5; The American Physical Society; Ridge, NY; US.
Groll, N., "On-Chip Cavity Studies of Spin Systems and Nonlinear Superconducting Phenomena for Quantum Computing Applications", The Florida State University DigiNole Commons, Electronic Theses, Treatises and Dissertations, Paper 3951, Oct. 22, 2010; Florida State University; Tallahassee, FL.
Hahn, E., "Concepts of NMR in Quantum Optics," Concepts in Magnetic Resonance, vol. 9(2), 1997, pp. 69-81; John Wiley & Sons, Inc.; Hoboken, NJ; US.
Hartman et al; "Nuclear Double Resonance in the Rotating Frame," Physical Review, vol. 128, No. 5; Dec. 1, 1962, pp. 2042-2053; the American Physical society, Ridge, NY; US.
Hauss, J. et al., "Single-Qubit Lasing and Cooling at the Rabi Frequency," Physical Review Letters 100, 037003, Jan. 25, 2008, pp. 1-4; The American Physical Society, Ridge, NY; US.
Hoult, D.I. and Ginsberg, N.S., "The Quantum Origins of the Free Induction Decay Signal and Spin Noise," Journal of Magnetic Resonance 148, 2001, pp. 182-199; Elsevier B.V.; Amsterdam, NL.
Jeener et al; "A presentation of pulsed nuclear magnetic resonance with full quantization of the radio frequency magnetic field," The Journal of Chemical Physics vol. 116, No. 18, May 8, 2002, pp. 8036-8047; AIP Publishing; Melville, NY; US.
Kubo, Y. et al., "Strong Coupling of a Spin Ensemble to a Superconducting Resonator," Physical Review Letters 105, 140502, Sep. 27, 2010, pp. 1-4; The American Physical Society; Ridge, NY; US.
Malissa, et al., "Superconducting Coplanar Waveguide Resonators for Low Temperature Pulsed Electron Spin Resonance Spectroscopy," Review of Scientific Instruments 84, 025116, Feb. 26, 2013, pp. 1-5; AIP Publishing; Melville, NY; US.
Mollow, B.R., "Power Spectrum of Light Scattered by Two-Level Systems," The Physical Review, Second Series, vol. 188, No. 5, Dec. 25, 1969, pp. 1969-1975; The American Physical Society; Ridge, NY; US.
Monroe, C. et al., "Resolved—Sideband Raman Cooling of a Bound Atom to the 3D Zero-Point Energy," Physical Review Letters, vol. 75, No. 22, Nov. 27, 1995, pp. 4011-4014; The American Physical Society, Ridge, NY; US.
Morton, J.J.L. et al., "Solid-state quantum memory using the 31P nuclear spin," Nature, vol. 455, Oct. 23, 2008, pp. 1085-1088; Macmillan Publishers Limited; London, UK.
Murch, K.W. et al., "Cavity-Assisted Quantum Bath Engineering," Physical Review Letters 109, 183602, Nov. 2, 2012, pp. 1-5; The American Physical Society; Ridge, NY; US.
Purcell, E.M., "Proceedings of the American Physical Society," Physical Review, vol. 69, Nos. 11 and 12, Jun. 1, 1946 Jun. 15, 1946, pp. 674-702; The American Physical Society; Ridge, NY; US.
Rabl, P. et al., "Hybrid Quantum Processors: molecular ensembles as quantum memory for solid state circuits," Physical Review Letters 97, 033003, Apr. 19, 2006, pp. 1-5; The American Physical Society; Ridge, NY; US.
Ramanathan, C., "Dynamic Nuclear Polarization and Spin Diffusion in Nonconducting Solids," Appl. Magn. Reson. (2008) 34, Jan. 5, 2008, pp. 409-421; Springer-Verlag; NL.
Ryan, C.A., et al., "Spin Based Heat Engine: Demonstration of Multiple Rounds of Algorithmic Cooling," Physical Review Letters 100, 140501, Apr. 2008, pp. 1-4; The American Physical Society; Ridge, NY; US.
Sakurai et al., "Modern Quantum Mechanics, Second Edition," Addison-Wesley, 1993, pp. 221-238; Pearson Education, Inc; San Francisco, CA.
Schuster, D.I. et al., "High-Cooperativity Coupling of Electron-Spin Ensembles to Superconducting Cavities," Physical Review Letters 105, 140501, Oct. 1, 2010, pp. 1-4; The American Physical Society, Ridge, NY; US.
Schwager, H., "Open quantum spin systems in semiconductor quantum dots and atoms in optical lattices", Dissertation, Technische Universitiit Mtinchen, Max-Planck-Institut fur Quantenoptik, Jul. 4, 2012, pp. 1-125; Munchen, DE.
Staudt, M.U. et al., "Coupling of an erbium spin ensemble to a superconducting resonator," Journal of Physics B: Atomic, Molecular, and Optical Physics 45, 124019, Jun. 8, 2012, pp. 1-5; IOP Publishing Ltd and Deutsche Physikalische Gessellschaft; Bristol, UK.
Tavis et al., "Approximate Solutions for an N-Molecule-Radiation-Field Hamiltonian," Physical Review, vol. 188, No. 2, Dec. 10, 1969, pp. 692-695; The American Physical Society; Ridge, NY; US.
Tavis et al., "Exact Solution for an N-Molecule-Radiation-Field Hamiltonian," Physical Review, vol. 170, No. 2, Jun. 10, 1968, pp. 379-384; The American Physical Society; Ridge, NY; US.
Terhal, Barbara M., "Quantum Error Correction for Quantum Memories," Institute for Quantum Information, Mar. 18, 2014, pp. 1-31; RWTH Aachen University, Aachen, Germany.
Torrezan, AC. et al., "Microstrip resonators for electron paramagnetic resonance experiments" , Review of Scientific Instruments 80, 075111, Jul. 31, 2009, pp. 16; American Institute of Physics; AIP Publishing; Melville, NY; US.
Tropp, J., "A quantum description of radiation damping and the free induction signal in magnetic resonance," The Journal of Chemical Physics 139, 014105, Jul. 2, 2013, pp. 1-8; AIP Publishing; Melville, NY; US.
Valenzuela, S. et al., "Microwave-Induced Cooling of a Superconducting Qubit," Science Magazine, vol. 314, Dec. 8, 2006, pp. 1589-1592; American Association for the Advancement of Science; Washington, DC; US.
Van Enk, S.J., et al.; "Cooling of a Single Atom in an Optical Trap inside a Resonator"; Physical Review A 64.1 013407; 15 pages; 2001; The American Physical Society; Ridge, NY; US.
Vuletic et al., "Laser Cooling of Atoms, Ions, or Molecules by Coherent Scattering," Physical Review Letters, vol. 84, No. 17, Apr. 24, 2000, pp. 37873790; The American Physical Society, Ridge, NY; US.
Wallquist, M. et al., "Theory of cavity-assisted microwave cooling of polar molecules," New Journal of Physics 10, 063005, Jun. 4, 2008, pp. 1-29; IOP Publishing Ltd and Deutsche Physikalische Gessellschaft; Bristol, UK.
Weber, J.R., et al., "Quantum computing with Defects," PNAS vol. 107, No. 19, May 11, 2010, pp. 8513-8518; Proceedings of the National Academy of Sciences of the United States of America; Washington, DC; US.
Wineland, D.J. and Itano, Wayne M., "Laser cooling of atoms," Physical Review A, vol. 20, No. 4, Oct. 1979, pp. 1521-1540; The American Physical Society; Ridge, NY; US.

(56) References Cited

OTHER PUBLICATIONS

Wood et al.; "Cavity Cooling of an Ensemble Spin System"; Physical Review Letters 112.5 050501; arXiv:1305.1029v2 [quant-ph]; 14 pages; Feb. 2014; The American Physical Society; Ridge, NY; US.
Xiang, Z-L. et al., "Hybrid quantum circuits: Superconducting circuits interacting with other quantum systems," Reviews of Modern Physics, vol. 85, Apr. 9, 2013, pp. 623-653; The American Physical Society; Ridge, NY; US.
Yamamoto et al; "Mesoscopic Quantum Optics," 1999, pp. 118-131; John Wiley & Sons, Inc., Hoboken, NJ; US.
European Patent Office, "Extended European Search Report", dated Feb. 17, 2017 in European Application No. 14791342.0, 7 pages.
European Patent Office, "Extended European Search Report", dated Feb. 17, 2017 in European Application No. 14791889.0, 9 pages.
Sienkiewicz, et al., "Tunable Q-band resonator for low temperature electron paramagnetic resonance/electron nuclear double resonance measurements", Review of Scientific Instruments, 67, 6, Jun. 1, 1996, pp. 2134-2138.
European Patent Office, Extended European Search Report dated May 30, 2017 in European Application No. 14791215.8, 10 pages.
European Patent Office, Extended European Search Report dated May 29, 2017 in European Application No. 14791139.0, 11 pages.
Abe, Eisuke, et al., "Electron Spin Ensemble Strongly Coupled to a Three-dimensional Microwave Cavity", arXiv:1106.0507v1 [quant-ph], Cornell University Library, Ithaca, NY, Jun. 2, 2011, 4 pages.
Butler, Mark, et al., "Polarization of nuclear spins by a cold nanoscale resonator", Physical Review A (Atomic, Molecular, and Optical Physics), vol. 84, No. 6, Dec. 1, 2011, 26 pages.
Francik, et al., "Q-band rectangular TE102 cavity for low-temperature EPR investigations", Inst. of Telecommun. & Acous., 32rd Polish Seminar on Nuclear Magnetic Resonance and its Applications, vol. 29, pp. 78-81, Molecular Physics Reports; ISSN 1505-1250, 2000, 1 page.
USPTO, Non-Final Office Action dated Apr. 12, 2018, in U.S. Appl. No. 14/787,624, 57 pgs.
JPO; Office Action issued in JP App. No. 2016-510909 dated Oct. 30, 2017, 3 pgs; with English translation (4 pages).
JPO, Office Action issued in JP App. No. 2016-510905 dated Oct. 30, 2017, 4 pgs; with English translation (4 pages).
European Patent Office, Extended European Search Report dated Jul. 6, 2017 in European Application No. 14791048.3, 8 pages.
USPTO, Non-Final Office Action dated Jan. 12, 2018, in U.S. Appl. No. 14/787,665, 17 pgs.
JPO; Office Action issued in JP App. No. 2016-510906 dated Nov. 6, 2017, 4 pgs.
JPO; Office Action issued in JP 2016-510904 dated Nov. 6, 2017, 5 pgs.
JPO; Office Action issued in JP2016-510903 dated Nov. 6, 2017, 6 pgs.
SIPO, Office Action dated Dec. 28, 2017, in CN App. 201480038040.3 with English translation, 18 pgs.
SIPO, Office Action dated Jan. 19, 2018, in CN App. No. 201480038188.7, with English translation, 24 pgs.
SIPO, Office Action dated Feb. 2, 2018, in CN201480038233.9 with English translation, 25 pgs.
USPTO, Non-Final Office Action dated Jan. 29, 2018, in U.S. Appl. No. 14/888,169, 42 pgs.
USPTO, Non-Final Office Action dated Mar. 1, 2018, in U.S. Appl. No. 14/888,180, 48 pgs.
SIPO, First Office Action dated Jan. 22, 2018, in CN App. No. 201480038230.5 with English translation, 15 pgs.
SIPO, Office Action dated Jan. 25, 2018, in CN App. 201480038202.3 with English translation, 21 pgs.
USPTO, Final Office Action dated Aug. 7, 2018, in U.S. Appl. No. 14/787,665, 25 pgs.
USPTO, Final Office Action dated Jul. 25, 2018, in U.S. Appl. No. 14/888,169, 25 pgs.
CNIPA, Second Office Action and Search Report dated Sep. 21, 2018, in CN 201480038040.3, 16 pgs.
CNIPA, Second Office Action and Supplementary Search Report dated Nov. 19, 2018, in CN201480038230.5, 17 pgs.

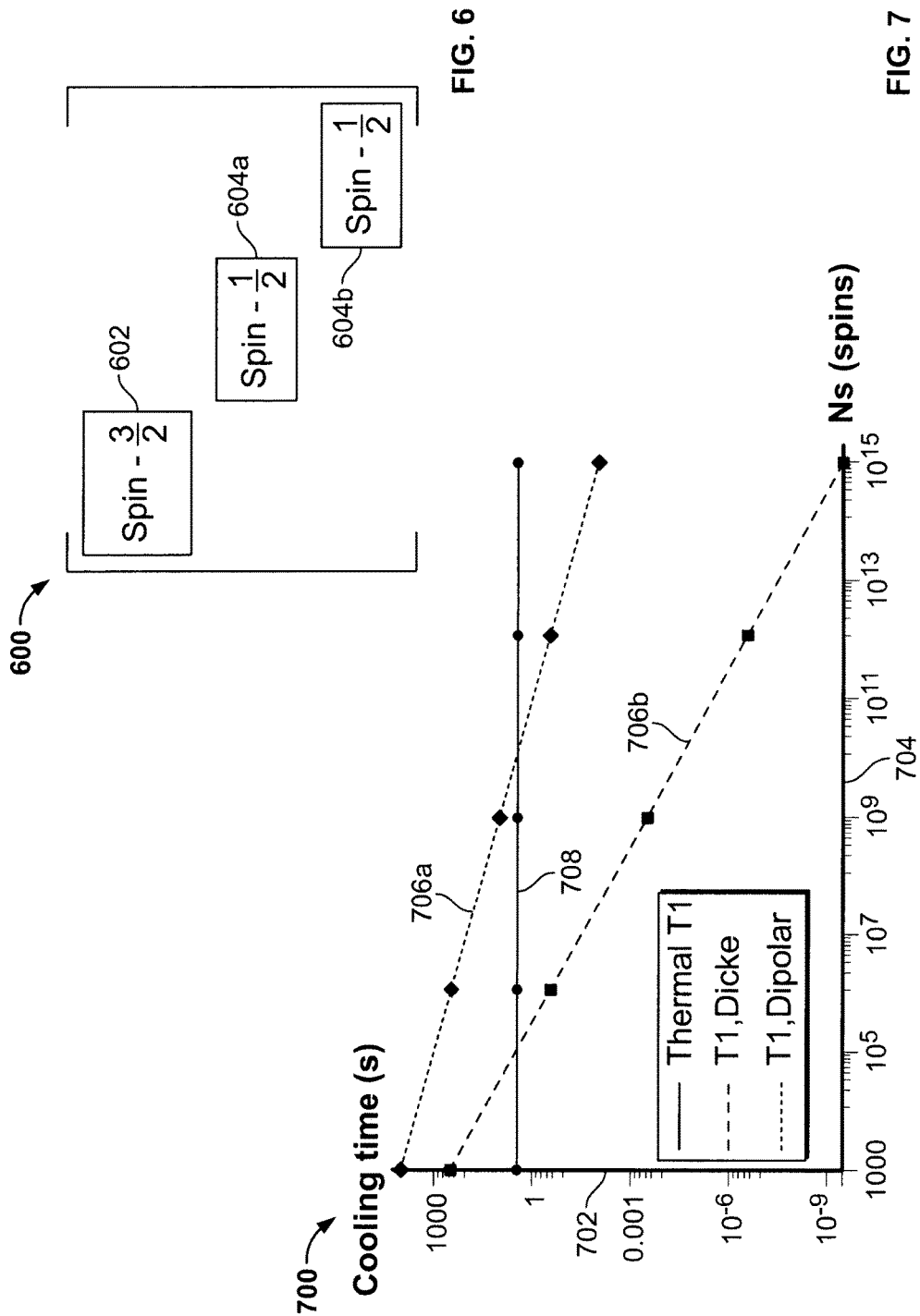

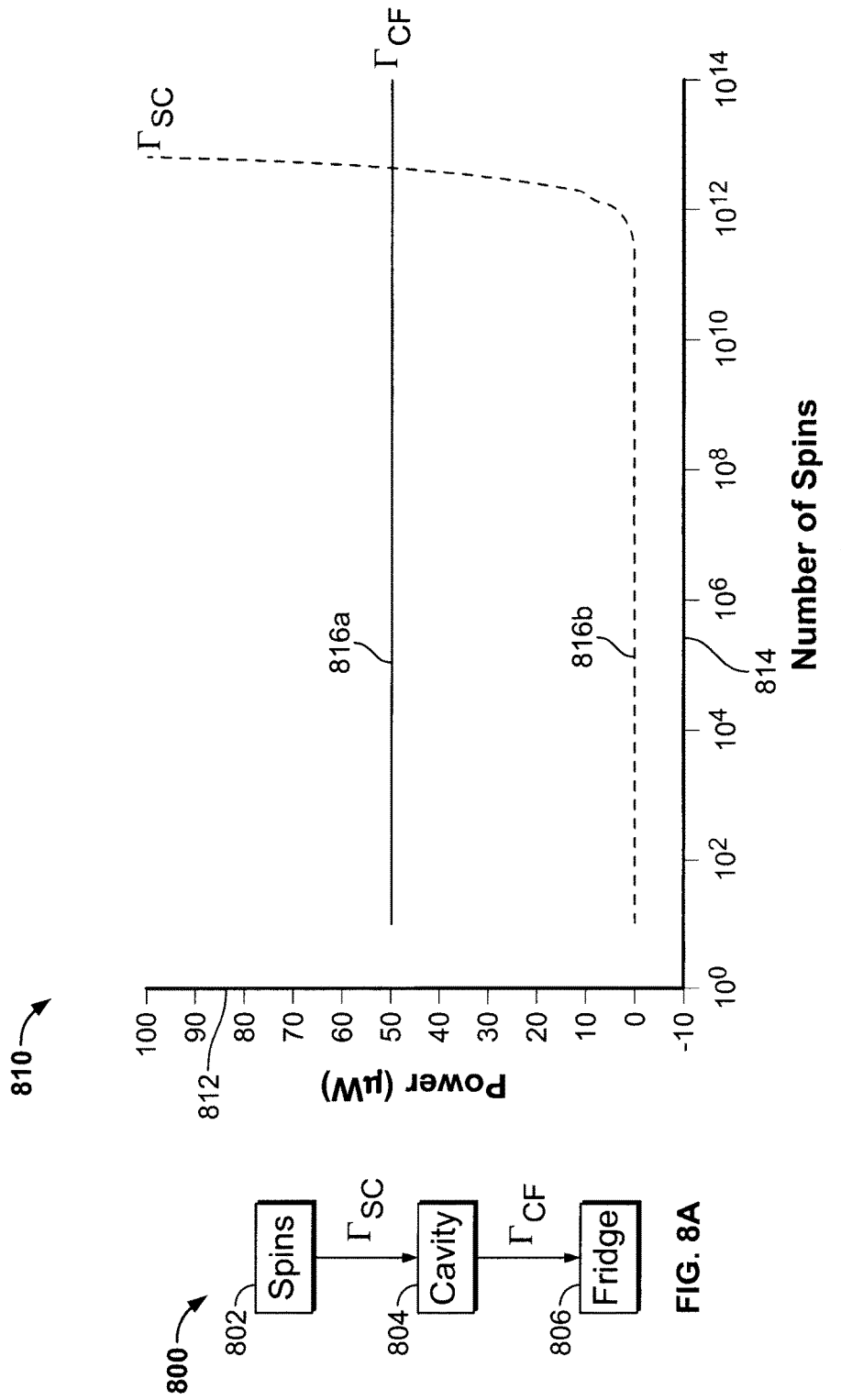

USING A CAVITY TO POLARIZE A SPIN ENSEMBLE

CLAIM OF PRIORITY

This application claims priority to U.S. Provisional Patent Application Ser. No. 61/819,103, filed on May 3, 2013, the entire contents of which are hereby incorporated by reference.

BACKGROUND

This document relates to using a cavity to increase spin polarization in magnetic resonance applications.

In magnetic resonance systems, signal-to-noise ratio (SNR) generally depends on the spin polarization and the time required to reach thermal equilibrium with the environment. The time required to reach thermal equilibrium—characterized by the energy relaxation time $T_1$—often becomes long, for example, at low temperatures. Conventional techniques for removing entropy from a quantum system include dynamic nuclear polarization (DNP), algorithmic cooling, optical pumping, laser cooling, and microwave cooling, among others.

Various approaches have been used to increase the signal-to-noise ratio (SNR) in magnetic resonance applications. For instance, signal averaging over multiple acquisitions is often used to increase SNR. Another approach is to increase the induction probe sensitivity, for example, by overlapping multiple induction coils and using phased array techniques. In some systems, induction probes are embedded in cryogens to reduce intrinsic noise within the induction probes.

SUMMARY

In some aspects, polarization of a spin ensemble is increased using cavity-based cooling techniques. A resonator applies a drive field to a spin ensemble in a static magnetic field. The drive field couples the spin ensemble with a cavity, and the coupling increases the polarization of the spin ensemble. In some cases, the cavity is detuned from the spin-resonance frequency, and the Rabi frequency associated with the drive field can be matched to the cavity detuning.

In some implementations, the polarization of the spin ensemble is increased by a coherent radiative interaction between the cavity and the spin ensemble. The interaction can increase the spin ensemble's polarization faster than an incoherent thermal process (e.g., thermal spin-lattice relaxation, spontaneous emission, etc.) affecting the spin ensemble.

In some implementations, cavity-based cooling can be made available on-demand and provide faster than thermal polarization. Increasing the spin ensemble's polarization may lead to an improved SNR, or other advantages in some cases.

The details of one or more implementations are set forth in the accompanying drawings and the description below. Other features, objects, and advantages will be apparent from the description and drawings, and from the claims.

DESCRIPTION OF DRAWINGS

FIG. 6 is a diagram of an example 3-spin Hilbert space.

FIG. 7 is a plot showing effective cooling times calculated for example spin ensembles.

FIG. 8A is a schematic diagram showing entropy flow in an example cavity-based cooling process.

FIG. 8B is a plot showing example values of the rates $\Gamma_{SC}$ and $\Gamma_{CF}$ shown in FIG. 8A.

Like reference symbols in the various drawings indicate like elements.

DETAILED DESCRIPTION

Here we describe techniques that can be used, for example, to increase the signal-to-noise ratio (SNR) in a magnetic resonance system by rapidly polarizing a spin ensemble. The techniques we describe can be used to achieve these and other advantages in a variety of contexts, including nuclear magnetic resonance (NMR) spectroscopy, electron spin resonance (ESR) spectroscopy, nuclear quadrupole resonance (NQR) spectroscopy, magnetic resonance imaging (MRI), quantum technologies and devices, and other applications.

We describe cavity-based cooling techniques applied to ensemble spin systems in a magnetic resonance environment. In some implementations, a cavity having a low mode volume and a high quality factor is used to actively drive all coupled angular momentum subspaces of an ensemble spin system to a state with purity equal to that of the cavity on a timescale related to the cavity parameter. In some instances, by alternating cavity-based cooling with a mixing of the angular momentum subspaces, the spin ensemble will approach the purity of the cavity in a timescale that can be significantly shorter than the characteristic thermal relaxation time of the spins ($T_1$). In some cases, the increase in the spin ensemble's polarization over time during the cavity-based cooling process can be modeled analogously to the thermal spin-lattice relaxation process, with an effective polarization rate ($1/T_{1,\textit{eff}}$) that is faster than the thermal relaxation rate ($1/T_1$).

Accordingly, the cavity can be used to remove heat from the spin ensemble (reducing the spin temperature) or to add heat to the spin ensemble (increasing the spin temperature), thereby increasing the spin polarization. Heating the spin ensemble can create an inverted polarization, which may correspond to a negative spin temperature.

Figure 1A:
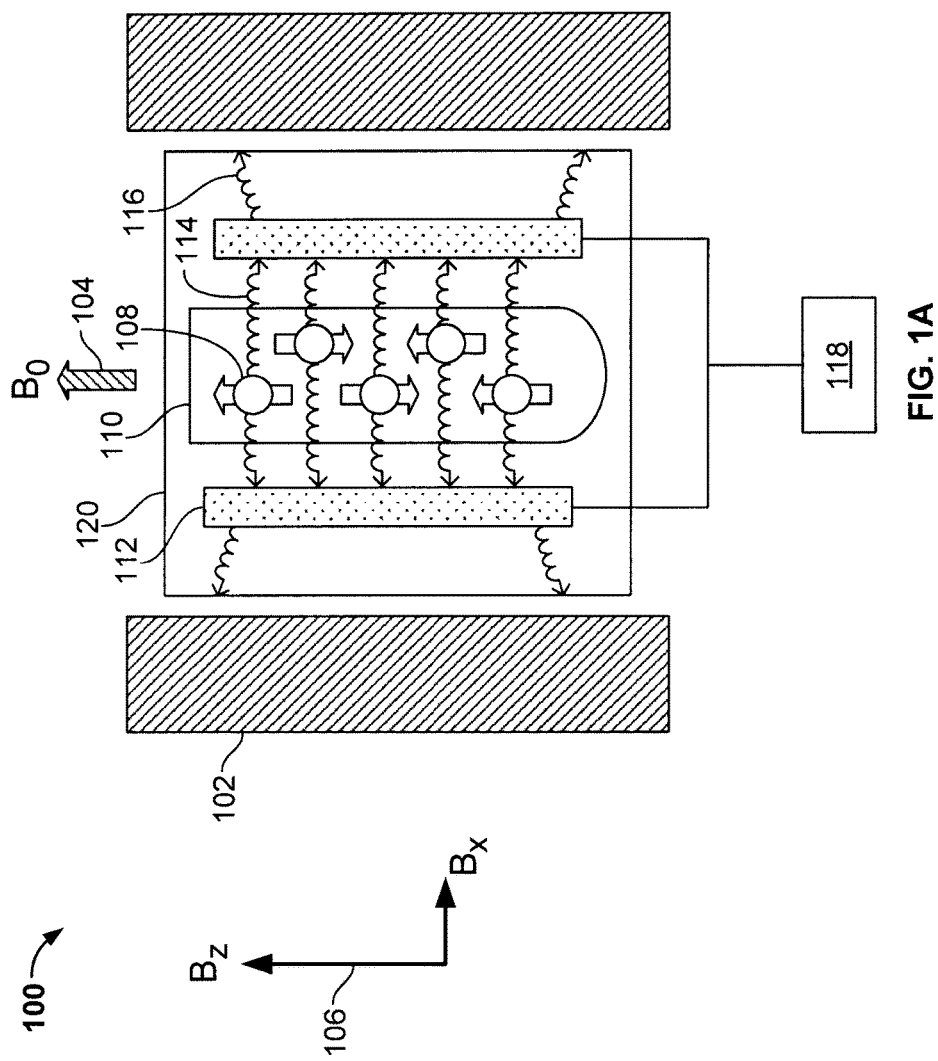
FIG. 1A is a schematic diagram of an example magnetic resonance system.

FIG. 1A is a schematic diagram of an example magnetic resonance system 100. The example magnetic resonance system 100 shown in FIG. 1A includes a primary magnet system 102, a cooling system 120, a resonator and cavity system 112, a sample 110 that contains spins 108, and a control system 118. A magnetic resonance system may include additional or different features, and the components of a magnetic resonance system can be arranged as shown in FIG. 1A or in another manner.

The example resonator and cavity system 112 can be used to control the spin ensemble as described in more detail below. In some cases, the cavity and resonator system 112 increases polarization of the spin ensemble by heating or cooling the spin ensemble.

The cooling system 120 provides a thermal environment for the resonator and cavity system 112. In some cases, the cooling system 120 can absorb heat from the cavity to maintain a low temperature of the cavity. The cooling system 120 may reside in thermal contact with the resonator and cavity system 112, the sample 110, or both. In some cases, the cooling system 120 maintains the resonator and cavity system 112, the sample 110, or both at liquid helium temperatures (e.g., approximately 4 Kelvin), at liquid nitrogen temperatures (e.g., approximately 77 Kelvin), or at another cryogenic temperature (e.g., less than 100 Kelvin). In some cases, the cooling system 120 maintains the resonator and cavity system 112, the sample 110, or both at pulsed-tube refrigerator temperatures (e.g., 5-11 Kelvin), pumped helium cryostat temperatures (e.g., 1.5 Kelvin), helium-3 fridge temperatures (e.g., 300 milliKelvin), dilution refrigerator temperatures (e.g., 15 milliKelvin), or another temperature.

In some cases, the resonator and the cavity are implemented as two separate structures, and both are held at the same cryogenic temperature. In some cases, the resonator and the cavity are implemented as two separate structures, and the cavity is held at a cryogenic temperature while the resonator is held at a higher temperature. In some cases, an integrated resonator/cavity system is held at a cryogenic temperature. In general, various cooling systems can be used, and the features of the cooling system 120 can be adapted for a desired operating temperature $T_C$, for parameters of the resonator and cavity system 112, or for other aspects of the magnetic resonance system 100.

In some implementations, the resonator and cavity system 112 operates at a desired operating temperature $T_C$ that is in the range from room temperature (approximately 300 K) to liquid helium temperature (approximately 4 K), and the cooling system 120 uses liquid-flow cryostats to maintain the desired operating temperature $T_C$. The cooling system 120 can include an evacuated cryostat, and the resonator and cavity system 112 can be mounted on a cold plate inside the cryostat. The resonator and cavity system 112 can be mounted in thermal contact with the cryostat, and it can be surrounded by a thermal radiation shield. The cooling system 120 can be connected to a liquid cryogen source (e.g., a liquid nitrogen or liquid helium Dewar) by a transfer line, through which the liquid cryogen can be continuously transferred to the cold head. The flow rate and liquid cryogen used can control the operating temperature. Gases can be vented through a vent.

In some cases, the cooling system 120 uses a closed-loop system (e.g., a commercial Gifford-McMahon pulsed-tube cryo-cooler) to maintain the desired operating temperature $T_C$ of the resonator and cavity system 112. A closed-loop or pulsed-tube system may, in some instances, avoid the need for continuously transferring costly liquid cryogen. In some closed-loop refrigerators, the cryostat has two-stages: the first stage (ranging, e.g., from 40 to 80 K) acts as a thermal insulator for the second stage, and the second stage encases the cold head and the resonator and cavity system 112. Some example closed-loop systems can reach a stable operating temperature of 10 Kelvin.

In some cases, the cooling system 120 uses a liquid helium cryostat to maintain the desired operating temperature $T_C$ of the resonator and cavity system 112. A liquid helium cryostat can be less complicated and more stable in some applications. When a liquid helium cryostat is used the resonator and cavity system 112 can be immersed (e.g., fully or partially immersed) in liquid helium. The system can include an outer Dewar that contains liquid nitrogen and an inner Dewar that contains liquid helium, and the two Dewars can be separated by a vacuum jacket or another thermal insulator. Liquid helium cryostat systems can typically reach a stable operating temperature of approximately 4 Kelvin.

In some cases, the cooling system 120 uses a helium-gas-flow (or pumped-helium) cryostat to maintain the desired operating temperature $T_C$ of the resonator and cavity system 112. Some commercial helium-gas-flow (or pumped-helium) cryostats can reach a stable operating temperature of 1.5 Kelvin. In such cases, the resonator and cavity system 112 can be mounted inside the cryostat, and a flow of helium gas can be communicated over the surface of the resonator and cavity system 112. In some implementations, the cooling system 120 includes a liquid helium Dewar that surrounds the resonator and cavity system 112 and is thermally isolated by a vacuum jacket, and a valve (e.g., a mechanically-controlled needle valve in the liquid helium Dewar) can control the flow of helium from the Dewar. The valve can control a port that opens into a gas heater, so that the liquid helium is vaporized and flows to the resonator and cavity system 112. The valve and heater can be externally controlled to provide the desired temperature regulation.

Some example helium-gas-flow cryostats can reach operating temperatures of 1 Kelvin by lowering the vapor pressure of the helium gas in the cryostat. This can be achieved by pumping on the helium in a small container (known as the "1-K pot") inside the vessel to lower the vapor pressure and thereby lower the boiling point of liquid helium (e.g., from 4.2 Kelvin down to 1 Kelvin). Some systems can cool down even further and reach milliKelvin temperatures, for example, using the helium-3 isotope (which is generally more expensive than the helium-4 isotope). The helium-3 can be pumped to much lower vapor pressures, thereby lowering the boiling point as low as 200 milliKelvin. A closed-loop system can be used to avoid leaks and preserve the helium-3 material.

In some cases, the cooling system 120 uses a dilution refrigerator system to maintain the desired operating temperature $T_C$ of the resonator and cavity system 112. Dilution refrigerator systems typically use a helium-3 circulation system that is similar to the helium-gas-flow cryostat described above. The dilution fridge system can pre-cool the helium-3 before entering the 1-K pot, to provide an operating temperature as low as 2 milliKelvin.

The magnetic resonance system 100 shown in FIG. 1A can polarize the spin ensemble in the sample 110. For example, the magnetic resonance system 100 can cool or map the spin ensemble to a thermal equilibrium state or to another state (i.e., a state other than the thermal equilibrium state, which may be more polarized or less polarized than the thermal equilibrium state).

In the example shown, the spins 108 in the sample 110 interact independently with the primary magnet system 102 and the resonator and cavity system 112. The primary magnet system 102 quantizes the spin states and sets the Larmor frequency of the spin ensemble. Rotation of the spin magnetization can be achieved, for example, by a radio-frequency magnetic field generated by a resonator. While the spins are weakly coupled to the environment, the cavity is well coupled to the environment (e.g., the cooling system 120) so that the time it takes for the cavity to reach thermal equilibrium is much shorter than the time it takes the spins to reach thermal equilibrium. The resonator can drive Rabi oscillations in the spin ensemble so that they couple to the cavity, and the Dicke states and other angular momenta subspaces of the spin system reach thermal equilibrium with the cavity.

The resonator and cavity system 112 can be described in terms of a cavity resonance and a spin resonance. The spin resonance is shifted from the cavity resonance by the Rabi frequency. The Rabi frequency (i.e., the frequency of the Rabi oscillations) can be a function of the power of the drive field applied at the spin-resonance frequency. The Rabi frequency can be configured to couple the spins to the cavity modes. For example, the power of the drive field can be set such that the Rabi frequency is substantially equal to the difference between the cavity resonance and the spin resonance. In some cases, the system can be modeled as a set of Dicke states and angular momenta subspaces of the spin ensemble (i.e., states in the Dicke and angular momenta subspace) coupled to the cavity modes through the Tavis-Cummings Hamiltonian.

A cavity having a low mode volume and high quality factor can produce a strong spin-cavity coupling for the spin ensemble. In some instances, the rate of photon exchange between the Dicke states and cavity scales as $\sqrt{N_s}$ (the number of spins in the spin ensemble) and g (the spin-cavity coupling strength for a single spin). In some examples, the spin-cavity coupling strength is inversely proportional to the square root of the mode volume and directly proportional to the square root of the admittance (i.e., the quality factor of the cavity).

In some implementations, the cavity is cooled efficiently and quickly, and the heat capacity of the cavity is large compared to the heat capacity of the spins. In some instances, the polarization rate produced by the spin-cavity interaction can be significantly faster than the thermal $T_1$ relaxation process. In some cases, the polarization rate produced by the spin-cavity interaction is faster than any internal relaxation process affecting the spin ensemble, including spontaneous emission, stimulated emission, thermal $T_1$ relaxation, or others. For example, as a result of the low mode volume and high quality factor cavity, the efficient cavity cooling, the efficient spin-cavity coupling, the mixing of angular momenta subspaces or a combination of these and other features, the spin ensemble can be cooled quickly toward the ground state. The mixing of angular momenta subspaces can be achieved, for example, by repeating a cavity-cooling process and using an interaction such as the Dipolar coupling, natural $T_2$ relaxation, external gradient fields, etc. In some aspects, this can provide an effective "short circuit" of the $T_1$ relaxation process. For example, the technique shown in FIG. 1C can be used to achieve faster spin polarization in some instances.

Figure 1B:
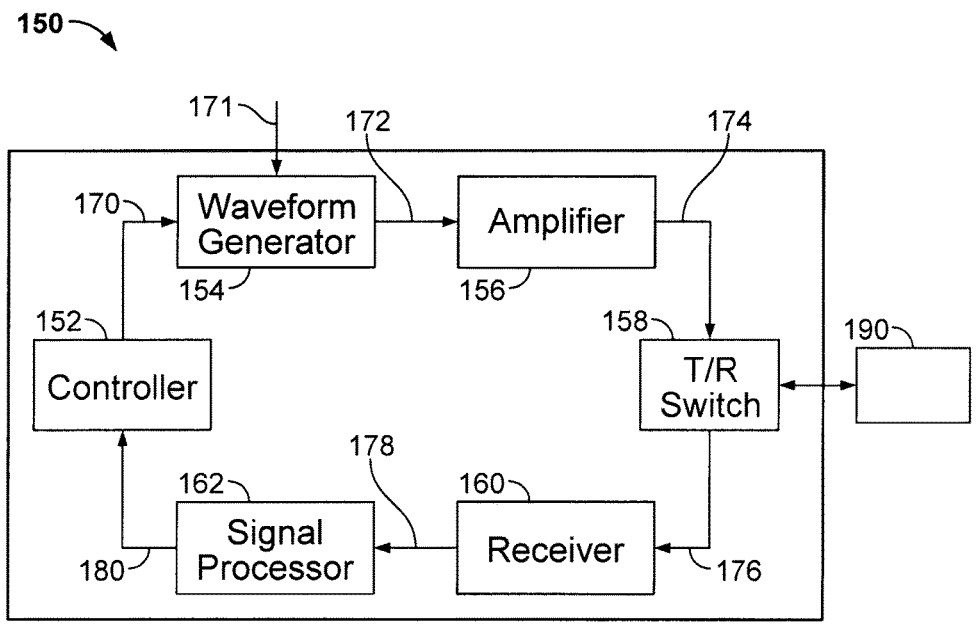
FIG. 1B is a schematic diagram of an example control system.
Figure 1C:
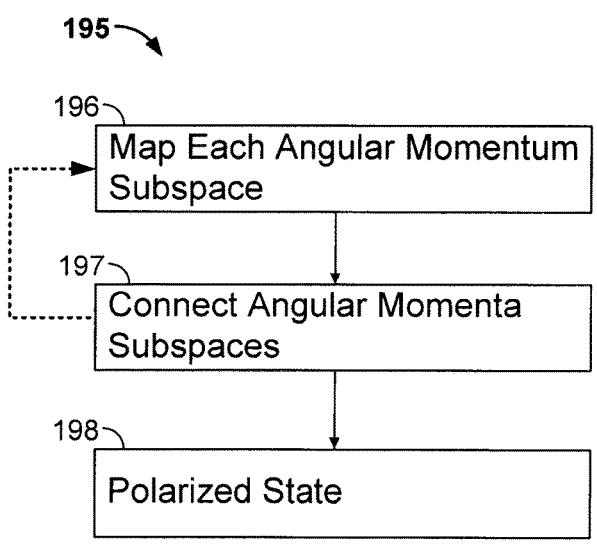
FIG. 1C is a flow chart of an example technique for increasing polarization of a spin ensemble.

FIG. 1C is a flow chart showing an example process 195 for increasing polarization of a spin ensemble. The example process 195 can be performed, for example, in the example magnetic resonance system 100 shown in FIG. 1A or in another type of system. The example process 195 shown in FIG. 1C can include additional or different operations. In some cases, individual operations can be divided into multiple sub-operations, or two or more of the operations can be combined or performed concurrently as a single operation. Moreover, some or all of the operations can be iterated or repeated, for example, until a desired state or polarization is achieved or until a terminating condition is reached.

As shown in FIG. 1C, at 196, angular momenta subspaces of a spin ensemble are mapped to a lower-energy state. For example, one or more angular momenta subspaces may be cooled to their respective lowest states. In some cases, a coherent interaction between the cavity and the spin ensemble can drive each angular momentum subspace to its lowest energy state. The mapping can be generated, for example, by applying a drive field to the spin ensemble. At 197, the angular momenta subspaces are connected. One or more of a number of different techniques can be used to connect the angular momenta subspaces. In some instances, the angular momenta subspaces are connected by a process that mixes the various subspaces of the overall space. For example, a dipolar interaction among spins, transverse ($T_2$) relaxation, an external gradient field, a similar external or internal dephasing interaction, or a combination of one or more of these can be used to connect the angular momenta subspaces. At 198, a more highly-polarized state is obtained. That is to say, the state of the spin ensemble can be more highly polarized than before the spin ensemble's angular momenta subspaces were cooled to their respective lowest states (at 196) and connected (at 197). The operations (196, 197) can be iterated one or more times, for example, until a desired polarization or other condition is reached.

In some implementations, the initial state of the spin ensemble (before 196) has less polarization than the spin ensemble's thermal equilibrium state. For example, the initial state of the spin ensemble may be a highly mixed state that has little or no polarization. The polarization of the state produced on each iteration can be higher than the polarization of the initial state. In some instances, the polarization is subsequently increased on each iteration. For example, the operations (196, 197) may be repeated until the spin ensemble reaches a thermal equilibrium polarization or another specified polarization level (e.g., an input polarization for a magnetic resonance sequence to be applied to the spin ensemble).

In some implementations, the process 195 can be used to polarize a spin ensemble on-demand. For example, the process 195 can be initiated at any time while the sample is positioned in the magnetic resonance system. In some cases, the spin ensemble is polarized between imaging scans or between signal acquisitions. Generally, the spin ensemble can be in any state (e.g., any fully or partially mixed state) when the process 195 is initiated. In some cases, the process 195 is initiated on-demand at a specified time, for example, in a pulse sequence, a spectroscopy or imaging process, or another process, by applying the Rabi field for a specified amount time.

In the example shown in FIG. 1A, the spin ensemble can be any collection of particles having non-zero spin that interact magnetically with the applied fields of the magnetic resonance system 100. For example, the spin ensemble can include nuclear spins, electron spins, or a combination of nuclear and electron spins. Examples of nuclear spins include hydrogen nuclei ($^1$H), carbon-13 nuclei ($^{13}$C), and others. In some implementations, the spin ensemble is a collection of identical spin-½ particles.

The example primary magnet system 102 generates a static, uniform magnetic field, labeled in FIG. 1A and referred here to as the $B_0$ field 104. The example primary magnet system 102 shown in FIG. 1A can be implemented as a superconducting solenoid, an electromagnet, a permanent magnet or another type of magnet that generates a static magnetic field. In FIG. 1A, the example $B_0$ field 104 is homogeneous over the volume of the sample 110 and oriented along the z direction (also referred to here as the "axial direction") of the axisymmetric reference system 106.

In the example system shown in FIG. 1A, interaction between the spins 108 and the primary magnet system 102 includes the Zeeman Hamiltonian $H=-\mu\cdot B$, where $\mu$ represents the magnetic moment of the spin and B represents the magnetic field. For a spin-½Particle, there are two states: the state where the spin is aligned with the $B_0$ field 104, and the state where the spin is anti-aligned with the $B_0$ field 104. With the $B_0$ field 104 oriented along the z-axis, the Zeeman Hamiltonian can be written $H=-\mu_z B_0$. Quantum mechanically, $\mu_z=\gamma\sigma_z$ where $\gamma$ is the spin gyromagnetic ratio and $\sigma_z$ is the z-direction spin angular momentum operator with angular momentum eigenstates $|m\rangle_s$ and eignevalues $m=\pm\frac{1}{2}\hbar$, where $\hbar$ is Planck's constant. The factor $\omega_s=\gamma B_0$ is the spin-resonance frequency also known as the Larmor frequency.

In the example shown in FIG. 1A, the thermal distribution of individual members of the ensemble being either aligned or anti-aligned with the $B_0$ field 104 is governed by Maxwell-Boltzmann statistics, and the density matrix for the thermal equilibrium state is given by $$\rho = \frac{1}{Z}e^{-H/kT},$$

where the denominator Z is the partition function, and H is the Hamiltonian of the spin ensemble. The partition function can be expressed $Z=\Sigma e^{-H/kT}$ where the sum is over all possible spin ensemble configurations. The constant k is the Boltzmann factor and T is the ambient temperature. As such, the thermal equilibrium state of the spin ensemble (and the associated thermal equilibrium polarization) can be determined at least partially by the sample environment (including the magnetic field strength and the sample temperature), according to the equation above. The polarization of the spin ensemble can be computed, for example, from the density matrix representing the state of the spin ensemble. In some instances, the spin polarization in the z-direction can be computed as the expectation value of the magnetization in the z-direction, $M_Z$, as follows:

$\langle M_Z \rangle = (\gamma\hbar)Tr\{J_Z\rho\}$ where $J_Z \equiv \Sigma_{j=1}^{N_s} \sigma_Z^{(j)}/2$ is the total spin ensemble z-angular momentum and $N_s$ is the ensemble spin size.

Once the spin ensemble has thermalized with its environment, any excitations that cause deviations away from thermal equilibrium will naturally take time (characterized by the thermal relaxation rate $T_1$) to thermalize. The thermal relaxation process evolves the spin ensemble from a non-thermal state toward the thermal equilibrium state at an exponential rate that is proportional to $1/T_1$. Many magnetic resonance applications manipulate the spins and acquire the inductive signals generated by them. Signal averaging is customarily used to improve the signal-to-noise ratio (SNR). However, the relaxation time $T_1$ may be relatively long and the efficiency of signal averaging is thereby reduced. In the example shown in FIG. 1A, the resonator and cavity system 112 can be used (e.g., in the example process 195 shown in FIG. 1C, or in another manner) to effectively "short-circuit" the relaxation process, which significantly reduces this wait time and increases the efficiency of signal averaging.

In some instances, the resonator and cavity system 112 can include a resonator component that controls the spin ensemble, and a cavity component that cools the spin ensemble. The resonator and cavity can be implemented as separate structures, or an integrated resonator/cavity system can be used. In some implementations, the resonator is tuned to a resonance frequency of one or more of the spins 108 in the sample 110. For example, the resonator can be a radio-frequency resonator, a microwave resonator, or another type of resonator.

The resonator and cavity system 112 is an example of a multi-mode resonance system. In some examples, a multi-mode resonance system has one or more drive frequencies, one or more cavity modes, and possibly other resonance frequencies or modes. The drive frequency can be tuned to the spins' resonance frequency, which is determined by the strength of the $B_0$ field 104 and the gyromagnetic ratio of the spins 108; the cavity mode can be shifted from the drive frequency. In some multi-mode resonance systems, the drive frequency and the cavity mode are provided by a single integrated structure. Examples of integrated multi-mode resonator structures include double-loop resonators, birdcage resonators, and other types of structures. In some multi-mode resonance systems, the drive frequency and cavity mode are provided by distinct structures. In some cases, the geometry of a low quality factor (low-Q) coil can be integrated with a high-Q cavity such that both the coil and cavity are coupled to the spin system but not to each other. The techniques described here can operate using a single drive frequency or possibly multiple drive frequencies applied to the coil.

In the example shown in FIG. 1A, the cavity has a resonance frequency $\omega_c$ that is different from the resonance frequency of the resonator. The cavity of the example resonator and cavity system 112 supports electromagnetic waves whose modes are determined by physical characteristics of the cavity. Typically, the fundamental mode is used as the cavity resonance and the quality factor of the cavity (Q) can be defined as the ratio of the stored energy in the cavity mode to the dissipated energy. In terms of frequency units, the quality factor of the cavity may be represented $$Q = \frac{\omega_c}{\Delta\omega},$$

where $\omega_c$ is the cavity-resonance frequency, and $\Delta\omega$ is the −3 dB bandwidth of the cavity resonance. In cases where the cavity resonance is given by a distribution that is Lorentzian, the bandwidth is given by the full-width at half-maximum (FWHM) of the cavity frequency response.

In some implementations, the cavity of the example resonator and cavity system 112 has a high quality factor (a high-Q cavity), so that an electromagnetic field in the cavity will be reflected many times before it dissipates. Equivalently, the photons in the cavity have a long lifetime characterized by the cavity dissipation rate $\kappa=(\omega/Q)$, where $\omega$ is the frequency of the wave. Such cavities can be made of superconducting material and kept at cryogenic temperatures to achieve quality factors that are high in value. For example, the quality factor of a high-Q cavity can have an order of magnitude in the range of $10^3$-$10^6$ or higher. Under these conditions, the electromagnetic field in the cavity can be described quantum mechanically as being equivalent to a quantum harmonic oscillator: a standard treatment known as cavity quantum electrodynamics or cavity QED. This treatment of the electromagnetic field in the cavity is in contrast to the Zeeman interaction where only the spin degree of freedom is quantum mechanical while the magnetic field is still classical.

For purposes of illustration, here we provide a quantum mechanical description of the cavity modes. Electromagnetic waves satisfy Maxwell's equations and both the electric field E and the magnetic field B can be described in terms of a vector potential A as $$B = \nabla \times A,$$
$$E = \frac{\partial A}{\partial t}.$$

The vector potential itself satisfies the wave equation $$\nabla^2 A = \frac{1}{c^2}\frac{\partial^2 A}{\partial t^2},$$

where c is the speed of light. The wave equation has a formal solution in the form of the Fourier series of plane waves:

$$A = \Sigma_k(A_k(t)e^{ik\cdot r} + A^*_k(t)e^{-ik\cdot r}),$$

where each Fourier component $A_k$ (t) also satisfies the wave equation. These plane waves are ones that the cavity supports in the case of cavity QED and by assuming $A_k(t)$ has time-dependence of the form $A_k(t) = A_k e^{i\omega_k t}$, the electric and magnetic fields are given by $$E_k = i\omega_k(A_k e^{-i\omega_k t + ik\cdot r} - A^*_k e^{i\omega_k t - ik\cdot r})$$

$$B_k = ik \times (A_k e^{-i\omega_k t + ik\cdot r} - A^*_k e^{i\omega_k t - ik\cdot r})$$

where the temporal and spatial frequencies ($\omega_k$ and k, respectively) are related by $\omega_k = ck$.

Accordingly, the energy of a single mode k is given by $$W_k = \tfrac{1}{2}\int dV(\epsilon_0 E_k^2 + \mu_0^{-1} B_k^2) = 2\epsilon_0 V \omega_k^2 A_k A^*_k,$$

where $\epsilon_0$ and $\mu_0$ are the permittivity and permeability of free space respectively, such that $c^2\mu_0\epsilon_0 = 1$ and V is the volume of space or cavity containing the radiation field. By defining the vector coefficients in terms of a real and imaginary part P and Q, we can express $A_k$ as:

$$A_k = (4\epsilon_0 V\omega_k^2)^{-1/2}(\omega_k Q_k + iP_k)\epsilon_k,$$

where $\epsilon_k$ is the polarization vector for the electromagnetic wave. In terms of $Q_k$ and $P_k$ the energy is given by $$W_k = \tfrac{1}{2}(P_k^2 + \omega_k^2 Q_k^2),$$

which is the form for the energy of a simple harmonic oscillator. Hence, we may treat the vectors $Q_k$ and $P_k$ of the electromagnetic wave as the position and momentum vectors of the Harmonic oscillator. This allows us to quantize the electromagnetic field in terms of single quanta (photons) by the standard canonical quantization of the harmonic oscillator.

We now consider the quantum treatment of a single electromagnetic mode in a cavity. The Hamiltonian for the quantum harmonic oscillator may be written in terms of the canonical P and Q variables as $$H = \tfrac{1}{2}(P^2 + \omega^2 Q^2).$$

We may then define operators $\alpha$ and $\alpha^+$, called the annihilation and creation operators, respectively, in terms of the vectors P and Q:

$$a = \sqrt{\frac{\omega}{2\hbar}}\left(Q + \frac{i}{\omega}P\right),$$

$$a^+ = \sqrt{\frac{\omega}{2\hbar}}\left(Q - \frac{i}{\omega}P\right).$$

These operators satisfy the commutation relation $[\alpha, \alpha^+] = 1$. Hence, our Hamiltonian may be written in terms of the creation and annihilation operators as $$H = \hbar\omega(\alpha^+\alpha + \tfrac{1}{2}).$$

The constant factor of a half corresponds to a constant energy shift of the cavity modes so we may remove it by going into an interaction frame which rescales the energies by this constant amount.

The energy eigenstates of this Hamiltonian are the so-called number states, which correspond to a single quanta (photon) of radiation within the cavity. They are labeled $|n\rangle_c$ where $n = [0, 1, 2, 3, \ldots]$. The action of the creation and annihilation operators on the number states is to create or remove a photon from the cavity:

$$\alpha|n\rangle_c = \sqrt{n}|n-1\rangle_c$$

$$\alpha^+|n\rangle_c = \sqrt{n+1}|n+1\rangle_c$$

Hence the operator $N = \alpha^+\alpha$ (the number operator) gives the total number of photons for a given number state:

$$\alpha^+\alpha|n\rangle_c = n|n\rangle_c.$$

The photon number state $|n\rangle_c$ is an energy eigenstate of the Hamiltonian $$H|n\rangle = \hbar\omega(n+1/2)|n\rangle_c,$$

with energy $(n+\tfrac{1}{2})\hbar\omega$.

We now describe how the cavity of the example resonator and cavity system 112 couples to the spin ensemble containing the spins 108. The dominant interaction is once again the spin magnetic dipole coupling to the cavity electromagnetic fields. Therefore, we have $$H_I = -\mu \cdot B,$$

and now the electromagnetic field of the cavity is treated quantum mechanically. In terms of the harmonic oscillator operators the magnetic field in the cavity can be written as $$B(r, t) = \sqrt{\frac{\mu_0 \hbar \omega}{2V}}(a - a^+)u(r, t)\epsilon$$

where $\epsilon$ is the propagation direction, $\mu_0$ is the free space permeability constant, $\hbar$ is the Planck constant, and the function u(r, t) represents the spatial and temporal wave behavior. For some examples, we take $\epsilon = \hat{x}$, and the function u (r, t) takes the form $$u(r,t) = u(r)\cos \omega t = u(y,z) \cos kx \cos \omega t,$$

where u(y,z) represents the cavity magnetic field spatial profile. In this form, the mode volume can be expressed $$V = \frac{\int |u(r)|^2 d^3r}{\max[|u(r)|^2]}.$$

As such, the mode volume is related to the spatial profile of the cavity magnetic field, and higher spatial homogeneity in the cavity magnetic field generally produces a lower mode volume. The spin-cavity interaction Hamiltonian then becomes $$H_I = \tfrac{1}{2} g \hbar (\alpha - \alpha^\dagger) \sigma_x,$$

where the constant g represents the coupling strength between each spin and the cavity, and $\sigma_x$ is the x-component spin angular momentum operator. The coupling strength can, in some instances, be defined by the expression $$g\hbar = -\mu \cdot |\langle 0|B|1\rangle| = \sqrt{\frac{\mu_0 \gamma^2 \hbar \omega}{2V}} \, |u(r)|.$$

In the example equations above, the spin-cavity coupling strength is inversely proportional to the square root of the mode volume.

The example resonator and cavity system 112 includes a resonator that can generate a Rabi field that is applied to the spin ensemble while the sample resides in the $B_0$ field 104. For example, the Rabi field can be a continuous field or a pulsed spin-locking field. In combination with the internal Hamiltonian of the spin system, the Rabi field can provide universal control of the spin ensemble. In some implementations, any magnetic resonance experiment or pulse sequence can be implemented in this manner. The resonator can generate the Rabi field, for example, based on signals from the control system 118, and the parameters of the field (e.g., the phase, power, frequency, duration, etc.) can be determined at least partially by the signal from the control system 118.

Figure 2:
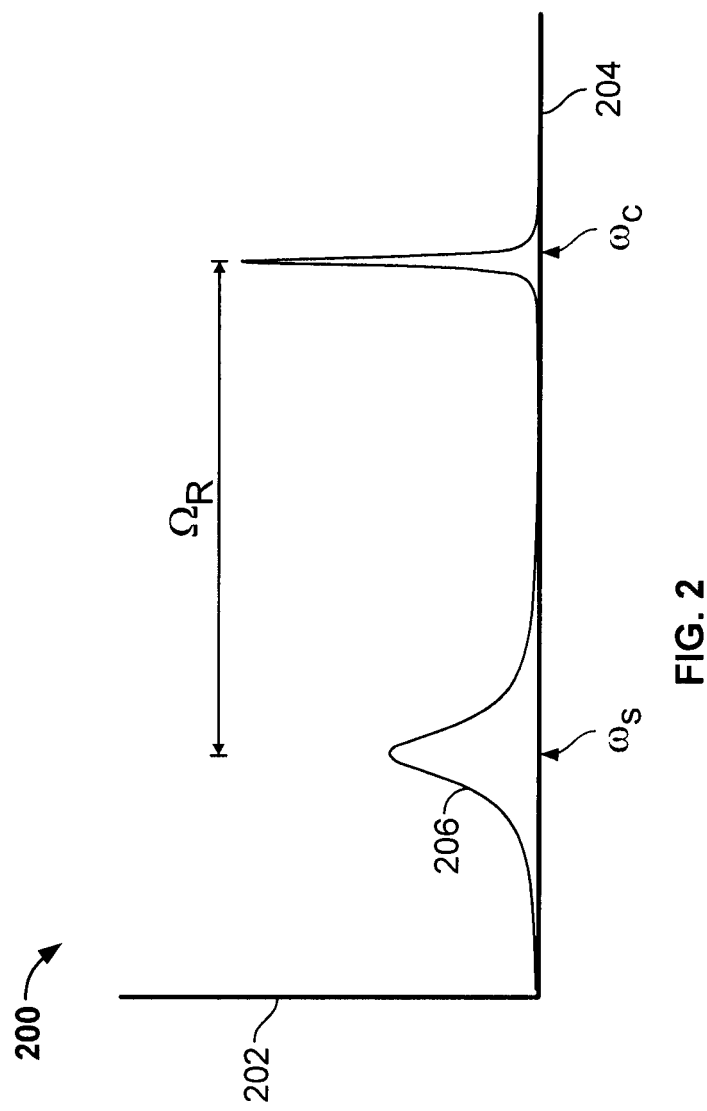
FIG. 2 is a plot showing a spin-resonance frequency, a cavity-resonance frequency, and a Rabi frequency in an example magnetic resonance system.

In the plot 200 shown in FIG. 2, the vertical axis 202 represents the frequency response of the resonator and the cavity, the horizontal axis 204 represents a range of frequencies, and the curve 206 shows the response shape for an example implementation of the resonator and cavity system 112. In the example shown, the lower frequency resonance (labeled $\omega_s$) is that of the resonator and the higher frequency resonance (labeled $\omega_c$) is that of the cavity. The quality factor (Q) of the cavity is higher than the quality factor (Q) of the resonator, and the resonance frequencies differ by the Rabi frequency (labeled $\Omega_R$).

The example control system 118 can control the resonator and cavity system 112 of the magnetic resonance system 100 shown in FIG. 1A. In some cases, the control system 118 can also control the cooling system 120 or other components of the magnetic resonance system 100. The control system 118 is electrically coupled to, and adapted to communicate with, the resonator and cavity system 112. For example, the control system 118 can be adapted to provide a voltage or current signal that drives the resonator, the cavity, or both; the control system 118 can also acquire a voltage or current signal from the resonator, the cavity, or both.

FIG. 1B is a schematic diagram of an example control system 150. The example control system 150 shown in FIG. 1B includes a controller 152, a waveform generator 154, and amplifier 156, a transmitter/receiver switch 158, a receiver 160, and a signal processor 162. A control system can include additional or different features, and the features of a control system can be configured to operate as shown in FIG. 1B or in another manner.

In the example shown in FIG. 1B, the example control system 150 is adapted to communicate with an external system 190. For example, the external system 190 can be a resonator, a cavity, or another component of a magnetic resonance system. The control system 150 can operate based on inputs provided by one or more external sources, including the external system 190 or another external source. For example, the control system can receive input from an external computer, a human operator, or another source.

The example control system 150 shown in FIG. 1B can operate in multiple modes of operation. In a first example mode of operation, the controller 152 provides a desired control operation 170 to the waveform generator 154. Based on the desired control operation 170, the waveform generator 154 generates a waveform 172. In some cases, the waveform generator 154 also receives system model data 171, and uses the system model data 171 to generate the waveform 172. The waveform 172 is received by the amplifier 156. Based on the waveform 172, the amplifier 156 generates a transmit signal 174. In this mode of operation, the transmitter/receiver switch 158 is configured to output the transmit signal 174 to the external system 190.

In a second example mode of operation, the transmitter/receiver switch 158 is configured to acquire a signal from the external system 190. The control system 150 can amplify, process, analyze, store, or display the acquired signal. As shown in FIG. 1B, based on the signal acquired from the external system 190, the transmitter/receiver switch 158 provides a received signal 176 to the receiver 160. The receiver 160 conditions the received signal 176 and provides the conditioned signal 178 to the signal processor 162. The signal processor 162 processes the conditioned signal 178 and generates data 180. The data 180 is provided to the controller 152 for analysis, display, storage, or another action.

The controller 152 can be (or include) a computer or a computer system, a digital electronic controller, a microprocessor or another type of data-processing apparatus. The controller 152 can include memory, processors, and may operate as a general-purpose computer, or the controller 152 can operate as an application-specific device.

We now show an example process by which the spin ensemble in the sample 110 can couple to the cavity and cool under a coherent Rabi drive. We start with an inductively driven ensemble of non-interacting spin-½ particles (represented in FIG. 1A by the spins 108) quantized in a large static magnetic field (represented in FIG. 1A by the $B_0$ field 104) and magnetically coupled to a high-Q cavity of the resonator and cavity system 112. In the presence of the drive provided by the resonator of the resonator and cavity system 112, the spins interact with the cavity via coherent radiative processes and the spin-cavity system can be treated quantum mechanically as a single collected magnetic dipole coupled to the cavity. In analogy to quantum optics, we describe the spin-cavity dynamics as being generated by the Tavis-Cummings (TC) Hamiltonian. Assuming the control field to be on resonance with the Larmor frequency of the spins, the spin-cavity Hamiltonian under the rotating-wave approximation (RWA) is given by $H = H_0 + H_R(t) + H_I$, with $$H_0 = \omega_c \alpha^\dagger \alpha + \omega_s J_z,$$

$$H_R(t) = \Omega_R \cos(\omega_s t) J_x, \text{ and}$$

$$H_I = g(\alpha^\dagger J_- + \alpha J_+).$$

As before, $\alpha^\dagger (\alpha)$ are the creation (annihilation) operators describing the cavity, $\Omega_R$ is the strength of the drive field (Rabi frequency), $\omega_c$ is the resonant frequency of the cavity, $\omega_s$ is the Larmor resonance frequency of the spins, and g is the coupling strength of the cavity to a single spin in the ensemble in units of $\hbar = 1$. Here we have used the notation that $$J_\alpha = \Sigma_{j=1}^{N_s} \sigma_\alpha^{(j)} / 2$$

are the total angular momentum spin operators for an ensemble of $N_s$ spins. The state-space V of a spin ensemble of $N_s$ identical spins may be written as the direct sum of coupled angular momentum subspaces $$V = \bigoplus_{J=j_0}^{\frac{N_s}{2}} V_J^{\oplus n_J}$$

where $j_0=0$ (½) if $N_s$ is even (odd). $V_J$ is the state space of a spin-J particle with dimension $d_J=2J+1$, and there are $n_J$ degenerate subspaces with the same total spin J. Since the TC Hamiltonian has a global SU(2) symmetry, it will not couple between subspaces in this representation. The largest subspace in this representation is called the Dicke subspace and consists of all totally symmetric states of the spin ensemble. The Dicke subspace corresponds to a system with total angular momentum $J=N_s/2$. The TC Hamiltonian restricted to the Dicke subspace is known as the Dicke model and has been studied for quantum optics.

The eigenstates of $H_0$ are the tensor products of photon-number states for the cavity and spin states of collective angular momentum of each total-spin subspace in the $J_z$ direction: $|n\rangle_c |J, m_z\rangle_s$. Here, $n=0,1,2, \ldots$, $m_z=-J, -J+1, \ldots, J-1, J$, and J indexes the coupled angular momentum subspace $V_J$. The collective excitation number of the joint system is given by $N_{ex}=\alpha^\dagger\alpha+(J_z+J)$. The interaction term $H_I$ commutes with $N_{ex}$, and hence preserves the total excitation number of the system. This interaction can drive transitions between the state $|n\rangle_c |J, m_z\rangle_s$ and states $|n+1\rangle_c |J, m_z-1\rangle_s$ and $|n-1\rangle_c |J, m_z+1\rangle_s$ at a rate of $\sqrt{(n+1)(J(J+1)-m_z(m_z-1))}$ and $\sqrt{n(J(J+1)-m_z(m_z+1))}$, respectively.

After moving into a rotating frame defined by $H_1=\omega_s(\alpha^\dagger\alpha+J_z)$, the spin-cavity Hamiltonian is transformed to $$\tilde{H}^{(1)}=e^{itH_1}H_{SC}e^{-itH_1}-H_1,$$

$$H^{(1)}=\delta\omega\alpha^\dagger\alpha+\Omega_R J_x+g(\alpha^\dagger J_-+\alpha J_+).$$

Here, $\delta\omega=\omega_c-\omega_s$ is the detuning of the drive from the cavity-resonance frequency, and we have made the standard rotating wave approximation (RWA) to remove any time dependent terms in the Hamiltonian.

If we now move into the interaction frame of $H_2=\delta\omega\alpha^\dagger\alpha+\Omega_R J_x/2$, the Hamiltonian transforms to $$\tilde{H}^{(2)}(t) = H_{0\Omega_R}(t) + H_{-\Omega_R}(t) + H_{+\Omega_R}(t)$$

$$H_{0\Omega_R}(t) = g(e^{-i\delta\omega t}a + e^{i\delta\omega t}a^\dagger)J_x$$

$$H_{-\Omega_R}(t) = \frac{ig}{2}(e^{-i(\delta\omega-\Omega_R)t}aJ_+^{(x)} - e^{i(\delta\omega-\Omega_R)t}a^\dagger J_-^{(x)})$$

$$H_{+\Omega_R}(t) = \frac{ig}{2}(e^{-i(\delta\omega+\Omega_R)t}aJ_-^{(x)} - e^{i(\delta\omega+\Omega_R)t}a^\dagger J_+^{(x)})$$

where $J_\pm^{(x)}\equiv J_y\pm iJ_z$ are the spin-ladder operators in the x-basis.

In analogy to Hartmann-Hahn matching in magnetic resonance cross-relaxation experiments for $\delta\omega>0$, we may set the cavity detuning to be close to the Rabi frequency of the drive, so that $\Delta=\delta\omega-\Omega_R$ is small compared to $\delta\omega$. By making a second rotating-wave approximation in the interaction Hamiltonian reduces to the $H_{-\Omega_R}$ flip-flop exchange interaction between the cavity and spins in the x-basis:

$$H_I(t) = \frac{ig}{2}(e^{i\Delta t}aJ_+^{(x)} - e^{-i\Delta t}a^\dagger J_-^{(x)})$$

This rotating-wave approximation is valid in the regime where the detuning and Rabi drive strength are large compared to the time scale, $t_c$, of interest ($\delta\omega, \Omega_R \gg 1/t_c$). From here we will drop the (x) superscript and just note that we are working in the $J_x$ eigenbasis for our spin ensemble.

Figure 3:
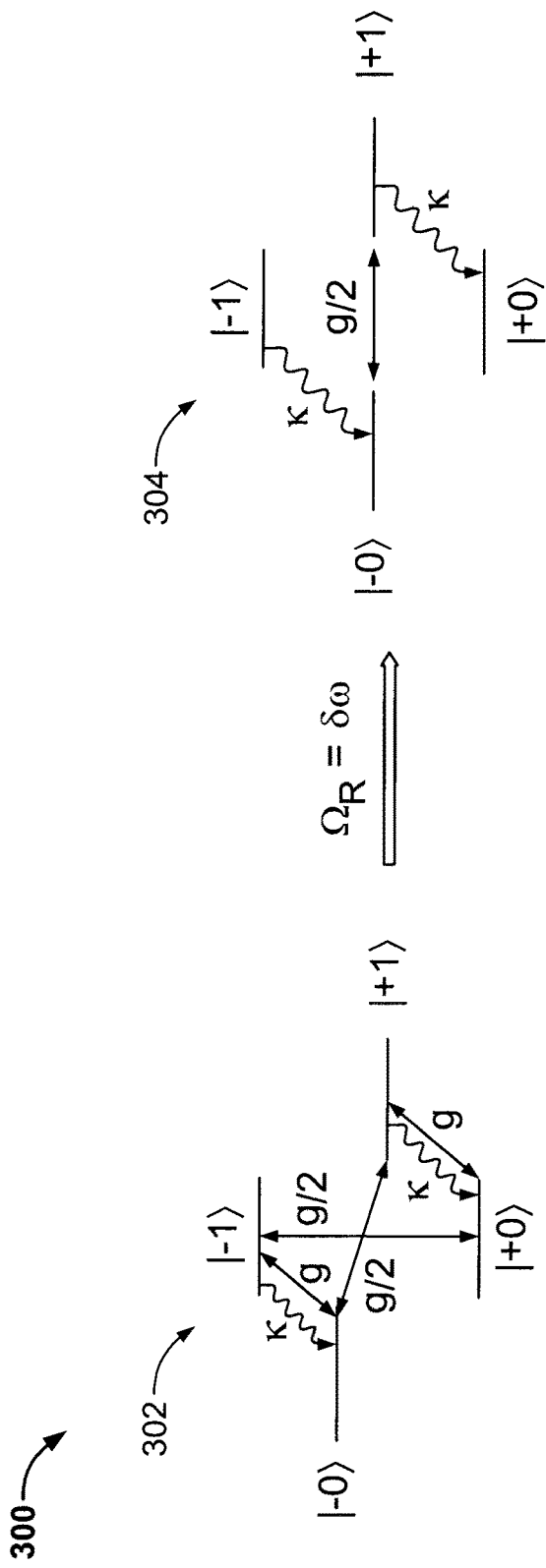
FIG. 3 shows two example energy level diagrams for a spin coupled to a two-level cavity.

In some implementations, isolating the spin-cavity exchange interaction allows efficient energy transfer between the two systems, permitting them to relax to a joint equilibrium state in the interaction frame of the control field. The coherent enhancement of the ensemble spin-cavity coupling can enhance spin polarization in the angular momenta subspaces $V_J$ at a rate greatly exceeding the thermal relaxation rate. FIG. 3 shows this coherent enhancement in terms of the coupled energy levels of the spin-cavity states.

FIG. 3 shows two example energy level diagrams 302, 304 for a spin coupled to a two-level cavity. In both diagrams, the ket $|+0\rangle$ represents the ground state of the spin-cavity system (where the spin and the cavity are in their respective ground states); the ket $|-1\rangle$ represents the excited state of the spin-cavity system (where the spin and the cavity are in their respective excited states), and the kets $|+1\rangle$ and $|-0\rangle$ represent intermediate states. In FIG. 3, the straight arrows represent coherent oscillations, and the curved arrows represent cavity dissipation.

FIG. 3 shows that when the cavity detuning is matched to the Rabi drive strength, energy exchange transitions between spin and cavity are enhanced. The energy level diagram 302 on the left shows the transitions without the coherent enhancement provided by the control drive. The energy level diagram 304 on the right shows the transition with the coherent enhancement provided by the control drive when $\Delta=\delta\omega-\Omega_R$ is small compared to $\delta\omega$. As shown in the energy level diagram 302 on the left, without the control drive all transition pathways are possible. The energy level diagram 304 on the right shows that when the Rabi drive is turned on and the cavity detuning is matched to the Rabi frequency, the energy exchange transitions between the spin and cavity are enhanced.

In the description below, to model the cavity-induced cooling of the spin system, we use an open quantum system description of the cavity and spin ensemble. The joint spin-cavity dynamics may be modeled using the time-convolutionless (TCL) master equation formalism, allowing the derivation of an effective dissipator acting on the spin ensemble alone. Since the spin-subspaces $V_J$ are not coupled by the TC Hamiltonian, the following derivation is provided for all values of J in the state-space factorization.

The evolution of an example spin-cavity system can be described by the Lindblad master equation $$\frac{d}{dt}\rho(t) = \mathcal{L}_I(t)\rho(t) + \mathcal{D}_c\rho(t),$$

where $\mathcal{L}_I$ is the super-operator $\mathcal{L}_I(t)\rho=-i[H_I(t), \rho]$ describing evolution under the interaction Hamiltonian and $\mathcal{D}_c$ is a dissipator describing the quality factor of the cavity phenomenologically as a photon amplitude damping channel:

$$\mathcal{D}_c = \frac{\kappa}{2}((1+\bar{n})D[a] + \bar{n}D[a^\dagger]).$$

Here, the function $D[A](\rho)=2A\rho A^\dagger-\{A^\dagger A, \rho\}$, $\bar{n}=\text{tr}[\alpha^\dagger\alpha\rho_{eq}]$ characterizes the temperature of the environment (e.g., the cooling system or other environment), and $\kappa$ is the cavity dissipation rate ($\propto 1/Q$). The expectation value of the number operator at equilibrium is related to the temperature $T_c$ of the environment by $$\bar{n} = (e^{\omega_c/k_B T} - 1)^{-1} \Leftrightarrow T = \frac{\omega_c}{k_B}\left[\ln\left(\frac{1+\bar{n}}{\bar{n}}\right)\right]^{-1},$$

where $k_B$ is the Boltzmann constant.

The reduced dynamics of the spin ensemble in the interaction frame of the dissipator is given to second order by the TCL master equation:

$$\frac{d}{dt}\rho_s(t) = \int_0^{t-t_0} d\tau \, tr_c[\mathcal{L}_I(t)e^{\tau D_c}\mathcal{L}_I(t-\tau)\rho_s(t)\otimes\rho_{eq}],$$

where $\rho_s(t)=tr_c[\rho(t)]$ is the reduced state of the spin ensemble and $\rho_{eq}$ is the equilibrium state of the cavity. Under the condition that $\kappa\gg g\sqrt{N_s}$, the master equation reduces to $$\frac{d}{dt}\rho_s(t) = \frac{g^2}{4}\int_0^{t-t_0} d\tau e^{-\kappa\tau/2}(\cos(\Delta\tau)\mathcal{D}_s\rho_s(t) - \sin(\Delta\tau)\mathcal{L}_s(t)\rho(t)),$$

where $\mathcal{D}_s = (1+\bar{n})D[J_-]+\bar{n}D[J_+]$, $\mathcal{L}_s\rho=-i[H_s, \rho]$, and $H_s=(1+\bar{n})J_-J_+ - \bar{n}J_-J_+$ are the effective dissipator and Hamiltonian acting on the spin ensemble due to coupling with the cavity.

Under the condition that $\kappa\gg g\sqrt{N_s}$ we may take the upper limit of the integral in the equation above to infinity to obtain the Markovian master equation for the driven spin ensemble:

$$\frac{d}{dt}\rho_s(t) = \left(\Omega_s\mathcal{L}_s + \frac{\Gamma_s}{2}\mathcal{D}_s\right)\rho_s(t)$$

where $$\Omega_s = -\frac{g^2\Delta}{\kappa^2+4\Delta^2}, \; \Gamma_s = \frac{g^2\kappa}{\kappa^2+4\Delta^2}.$$

Here, $\Omega_s$ is the frequency of the effective Hamiltonian, and $\Gamma_s$ is the effective dissipation rate of the spin-system.

We can consider the evolution of a spin state that is diagonal in the coupled angular momentum basis, $\rho(t)=\Sigma_J\Sigma_{m=-J}^{J}P_m(t)\rho_{J,m}$. Here, the sum over J is summing over subspaces $V_J$, and $P_{J,m}(t)=\langle J, m|\rho(t)|J, m\rangle$ is the probability of finding the system in the state $\rho_{J,m}=|J, m\rangle\langle J, m|$ at time t. In this case the Markovian master equation reduces to a rate equation for the populations:

$$\frac{d}{dt}P_{J,m}(t) = \Gamma_s(A_{J,m+1}P_{J,m+1}(t) + B_{J,m}P_{J,m}(t) + C_{J,m-1}P_{J,m-1}(t)),$$

where $A_{J,m}=(1+\bar{n})[J(J+1)-m(m-1)]$ $C_{J,m}=\bar{n}[J(J+1)-m(m+1)]$, and $B_{J,m}=-(A_m+C_m)$.

Defining $\vec{P}_J(t)=(P_{J,-J}(t), \ldots, P_{J,J}(t))$, we obtain the following matrix differential equation for each subspace $V_J$:

$$\frac{d}{dt}\vec{P}_J(t) = \Gamma_s M_J \vec{P}_J(t),$$

where $M_J$ is the tridiagonal matrix $$M_J = \begin{pmatrix} B_{J,-J} & A_{J,-J+1} & 0 & 0 & 0 & \ldots & 0 \\ C_{J,-J} & B_{J,-J+1} & A_{J,-J+2} & 0 & 0 & \ldots & 0 \\ 0 & C_{J,-J+1} & B_{J,-J+2} & A_{J,-J+3} & 0 & \ldots & 0 \\ \vdots & & & \ddots & & & \vdots \\ 0 & & \ldots & & 0 & C_{J,J-1} & B_{J,J} \end{pmatrix}.$$

For a given state specified by initial populations $\vec{P}_J(0)$, the above differential equation has the solution $\vec{P}_J(t)=\exp(t\Gamma_s M_J)\vec{P}_J(0)$. The equilibrium state of each subspace $V_J$ of the driven spin ensemble satisfies $M_J\vec{P}_J(\infty)=0$, and is given by $\rho_{J, eq}=\Sigma_{m=-J}^{J}P_{J,m}(\infty)\rho_{J,m}$, where $$P_{J,m}(\infty) = \frac{\bar{n}^{J+m}(1+\bar{n})^{J-m}}{(1+\bar{n})^{2J+1}-\bar{n}^{2J+1}}.$$

The total spin expectation value for the equilibrium state of the spin ensemble is $$\langle J_x\rangle_{eq} = -J + \bar{n} - \frac{(2J+1)\bar{n}^{2J+1}}{(1+\bar{n})^{2J+1}-\bar{n}^{2J+1}}.$$

If we consider the totally symmetric Dicke subspace in the limit of $N_s\gg\bar{n}$, we have that the ground state population at equilibrium is given by $P_{N_s/2,-N_s/2}\approx 1/(1+\bar{n})$ and the final expectation value is approximately $\langle J_x\rangle_{eq}\approx -N_s/2+\bar{n}$. Thus, the final spin polarization in the Dicke subspace will be roughly equivalent to the thermal cavity polarization.

We note that, if the detuning $\delta\omega$ were negative in the example described above, matching $\Omega_R=\delta\omega$ would result in the $H_{+\Omega_R}$ term being dominant, leading to a master equation with the operators $J_-$ and $J_+$ interchanged, the dynamics of which would drive the spin ensemble towards the $\langle J_x\rangle=J$ state. The detuning can be made larger than the cavity linewidth to prevent competition between the $H_{-\Omega_R}$ and $H_{+\Omega_R}$ terms, which would drive the spin system to a high entropy thermally mixed state.

In some implementations, the cavity-resonance frequency ($\omega_c$) is set below the spin-resonance frequency ($\omega_s$) such that the detuning $\delta\omega=\omega_c-\omega_s$ is a negative value. In such cases, the techniques described here can be used to perform cavity-based heating of the spins to increase the polarization of spin ensemble. In such cases, the energy of the spin ensemble is increased by the interaction between the cavity and the spin ensemble.

The tridiagonal nature of the rate matrix allows $P_J(t)=\exp(t\Gamma_s M_J)\vec{P}_J(0)$ to be efficiently simulated for large numbers of spins. For simplicity we will consider the cooling of the Dicke subspace in the ideal case where the cavity is cooled to its ground state ($\bar{n}=0$), and the spin ensemble is taken to be maximally mixed (i.e., $P_m(0)=1/(2J+1)$ for $m=-J, \ldots, J$).

Figure 4:
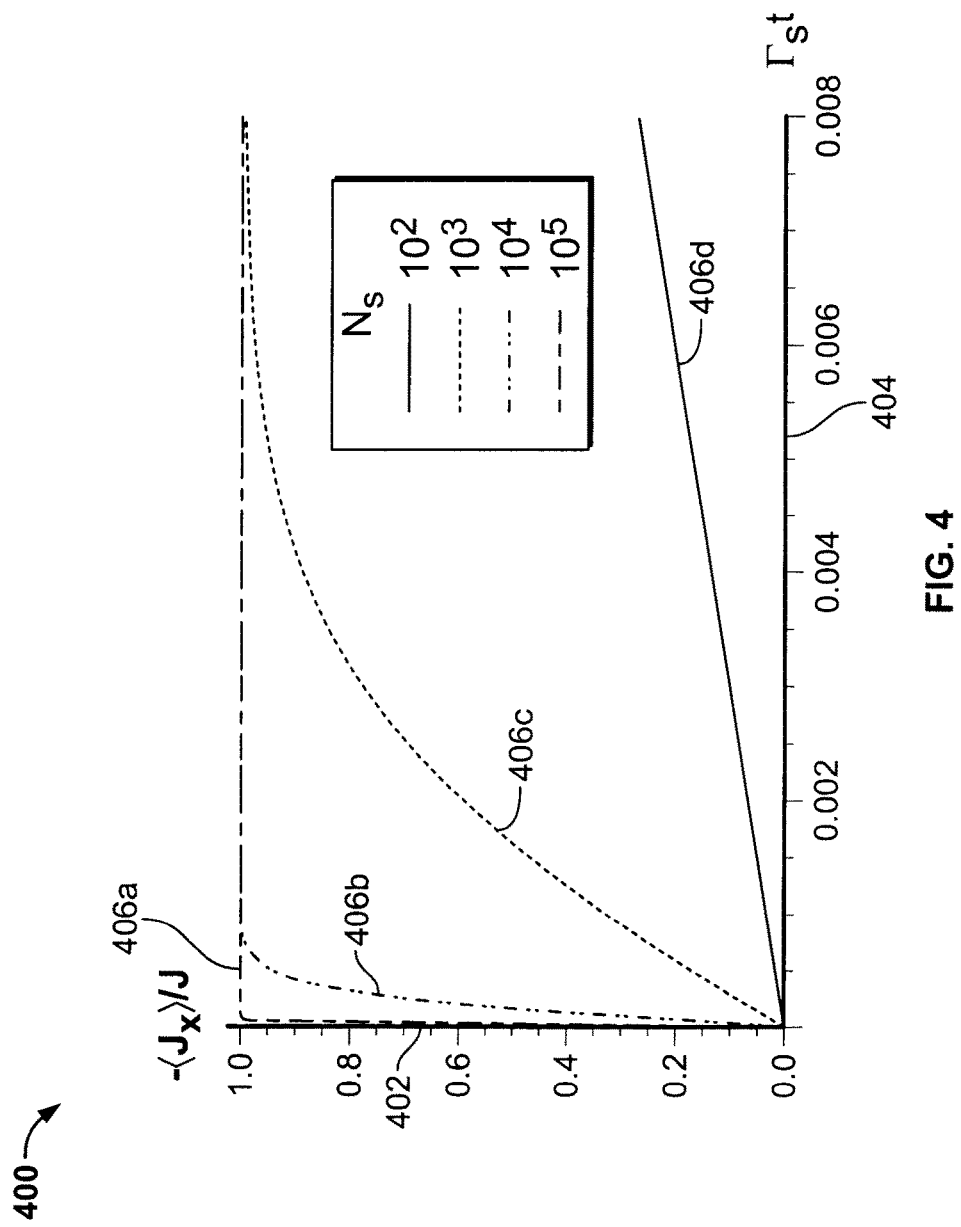
FIG. 4 is a plot showing simulated evolution of the normalized expectation value of $-\langle J_x(t)\rangle/J$ for the Dicke subspace of an example cavity-cooled spin ensemble.

FIG. 4 is a plot 400 showing simulated evolution of the normalized expectation value of $-\langle J_x(t)\rangle/J$ for the Dicke subspace of an example cavity-cooled spin ensemble. In the plot 400, the vertical axis 402 represents a range of values of the normalized expectation value of $-\langle J_x(t)\rangle/J$ for the Dicke subspace, and the horizontal axis 404 represents a range of time values. In FIG. 4, the expectation values represented by the vertical axis 402 are normalized by $-J$ to obtain a maximum value of 1, and the time variable represented by the horizontal axis 404 is scaled by the effective dissipation rate $\Gamma_s$ for the spin ensemble.

The plot 400 includes four curves; each curve represents the simulated expectation value of $\langle J_x(t)\rangle$ for the Dicke subspace of a spin ensemble with a different number of total spins $N_s$, ranging from $N_s=10^2$ to $N_s=10^5$. The curve 406a represents a spin ensemble of $10^2$ spins; the curve 406b represents a spin ensemble of $10^3$ spins; the curve 406c represents a spin ensemble of $10^4$ spins; and the curve 406d represents a spin ensemble of $10^5$ spins.

At a value of $-\langle J_x(t)\rangle/J=1$, the total angular momentum subspace of the spin ensemble is completely polarized to the $J_x$ ground eigenstates $|J, -J\rangle$. As shown in FIG. 4, the polarization of each spin ensemble increases over time, and the polarization increases faster for the larger spin ensembles. For the examples shown, the three larger spin ensembles are substantially fully polarized within the timescale shown in the plot 400.

In some cases, the expectation value $\langle J_x(t)\rangle$ versus time can be fitted to an exponential to derive an effective cooling time-constant, $T_{1,\mathit{eff}}$, analogous to the thermal spin-lattice relaxation time $T_1$. A fit to a model given by $$-\frac{\langle J_x(t)\rangle}{J} = 1 - \exp\left(-\frac{t}{T_{1,\mathit{eff}}}\right)$$

yields the parameters $T_{1,\mathit{eff}}=\lambda(2J)^\gamma/\Gamma_s$, with $\lambda=2.0406$ and $\gamma=-0.9981$. This model includes an exponential rate ($1/T_{1,\mathit{eff}}$), analogous to the thermal spin-lattice relaxation process, which includes an exponential rate ($1/T_1$). This model can be used for an angular momentum subspace (e.g., the Dicke subspace) or the full Hilbert space. In some instances, the effective rate ($1/T_{1,\mathit{eff}}$) is significantly faster than the thermal rate ($1/T_1$). An approximate expression for the cooling-time constant for the spin subspace $V_J$ as a function of J is $$T_{1,\mathit{eff}}(J) \approx \frac{2}{\Gamma_s J_s} = \frac{2(\kappa^2+4\Delta^2)}{g^2\kappa J}.$$

In this effective cooling time-constant, the cooling efficiency is maximized when the Rabi drive strength is matched to the cavity detuning (i.e., $\Delta=0$). In this case, the cooling rate and time-constant simplify to $\Gamma_s=g^2/\kappa$ and $T_{1,\mathit{eff}}=\kappa/g^2J$, respectively. In the case where the cavity is thermally occupied, the final spin polarization is roughly equal to the thermal cavity polarization, and for cavity temperatures corresponding to $\bar{n}<\sqrt{2J}$ the effective cooling constant $T_{1,\mathit{eff}}$ is approximately equal to the zero temperature value.

A magnetic resonance system can be controlled in a manner that polarizes a sample at a rate corresponding to the effective cooling constant $T_{1,\mathit{eff}}$ shown above. The magnetic resonance system can be configured according to the parameters that adhere to the two rotating wave approximations used to isolate the spin-cavity exchange term $H_I(t)$. For implementations where $\delta\omega\approx\Omega_R$, the magnetic resonance system can be configured such that $g\sqrt{N_s}\ll\kappa\ll\Omega_R$, $\delta\omega\ll\omega_c, \omega_s$.

For an example implementation using X-band pulsed electron spin resonance (ESR) ($\omega_c/2\pi\approx\omega_s/2\pi=10$ GHz) with samples that contain from roughly $N_s=10^6$ spins to $N_s=10^{17}$ spins, the magnetic resonance system can be configured such that $\Omega_R/2\pi=100$ MHz, $Q=10^4$ ($\kappa/2\pi=1$ MHz) and $g/2\pi=1$ Hz. For these parameters, the range of validity of the Markovian master equation is $N_s\ll\kappa^2/g^2=10^{12}$ and the Dicke subspace of an ensemble containing roughly $10^{11}$ electron spins may be polarized with an effective $T_1$ of 3.18 μs. This polarization time is significantly shorter than the thermal $T_1$ for low-temperature spin ensembles, which can range from seconds to hours.

Figure 5:
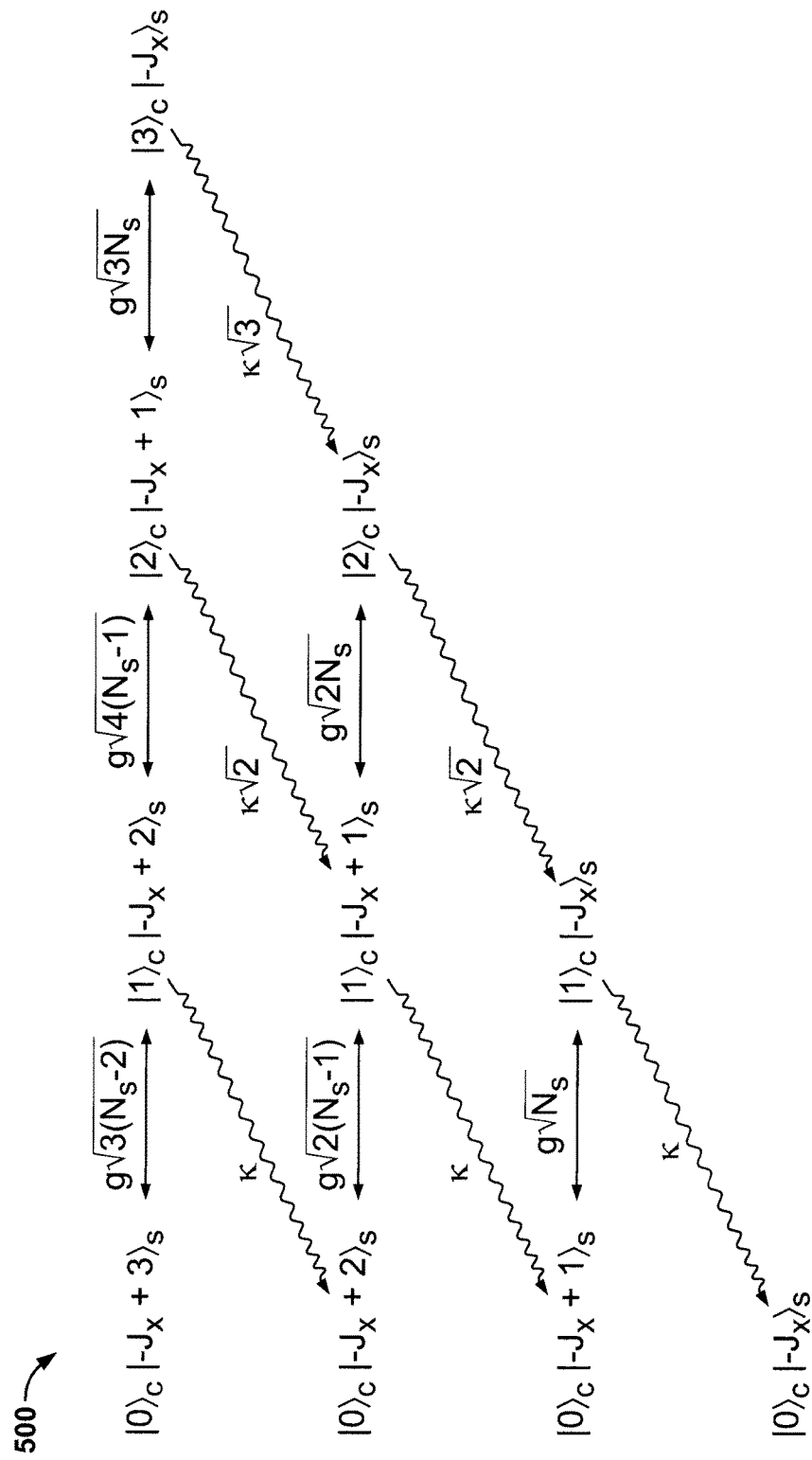
FIG. 5 is an energy level diagram of an example spin system coupled to a two-level cavity.

FIG. 5 is an energy level diagram 500 of an example spin system coupled to a two-level cavity. Coherent transitions are denoted by a solid line and cavity dissipation rates are denoted by a curved line. States in each subspace $V_J$ are labeled $|n\rangle_c|-J_x+m\rangle_s$, where m is the number of spin excitations and n is the number of cavity excitations. Within each subspace $V_J$, for cooling dynamics to appear Markovian, states of high cavity excitation number should not be significantly populated on a coarse-grained timescale.

In the examples shown here, the spin ensemble is cooled by a coherent interaction with the cavity, which increases the polarization of the spin ensemble. These cavity-based cooling techniques are different from thermal $T_1$ relaxation, for example, because the cavity-based techniques include coherent processes over the entire spin ensemble. Thermal $T_1$ relaxation is an incoherent process that involves exchanging energy between individual spins and the environment, which is weakly coupled when $T_1$ is long. Cavity-based cooling techniques can provide a controlled enhancement of the spins' coupling to the thermal environment, by using the cavity as a link between the spin ensemble and the environment. The cavity is more strongly coupled to the environment than the spin ensemble, so energy in the form of photons is dissipated more quickly. Due to the inherently small coupling of an individual spin to the cavity, the cavity can be efficiently coupled to the spin ensemble by driving the spin ensemble so that it interacts collectively with the cavity as a single dipole moment with a greatly enhanced coupling to the cavity. In some cases, the resulting link between the spin ensemble and environment—going through the cavity—is significantly stronger than the link between the spin ensemble and the environment in the absence of the cavity, resulting in higher efficiency of energy dissipation from the spin ensemble when using the cooling algorithm, and a shorter effective $T_1$.

The discussion above shows how the Dicke subspace and the other subspaces are polarized by cavity-based cooling techniques. We now describe how the entire state can be cooled. Due to a global SU(2) symmetry, the state space of the spin ensemble factorizes into coupled angular momentum subspaces for the spins. The largest dimension subspace is called the Dicke subspace (which corresponds to an angular momentum J=N/2, where N is the number of spins). For example:

2 spins: (Spin-1/2)$^{\otimes 2}$ →Spin-1 (triplet)⊕Spin-0 (singlet)

3 spins: (Spin-1/2)$^{\otimes 2}$ →Spin-3/2⊕Spin-1/2⊕Spin-1/2.

As shown in FIG. 6, in the 3-spins case, the spin-3/2 subspace has the largest dimension and thus is the Dicke subspace.

FIG. 6 is a diagram 600 of an example state space represented as a 3-spin Hilbert space. The diagram 600 is a matrix representation of the 3-spin Hilbert space. The matrix has a block-diagonal form, where each block along the diagonal represents a distinct subspace. The first block represents a spin-3/2 subspace 602, and the second and third blocks represent two spin-1/2subspaces 604a, 604b. In FIG. 6, the spin-3/2 subspace 602 is the Dicke subspace because it is the subspace of largest dimension. Cavity-based cooling can cool each respective subspace to its respective ground state. An interaction that breaks the SU(2) symmetry of the Hilbert space can couple the distinct subspaces, and cavity-based cooling can cool the spin system to the true ground state of the entire Hilbert space. In the example 3-spins case shown in FIG. 6, the true ground state resides in the spin-3/2subspace 602.

Cavity-based cooling can act independently on each subspace, cooling each subspace to its respective ground state with an effective relaxation time of $$T_{1,J} = \frac{1}{\Gamma_s J},$$

where J is the spin of the subspace, and $\Gamma_s$ is the cavity-cooling rate derived from the Markovian master equation. In some examples, the true ground state of the spin ensemble is the state where all spins are either aligned or anti-aligned with the $B_0$ field, and that state is in the Dicke subspace. Generally, at thermal equilibrium the spin ensemble will be in a mixed state, and there will be a distribution of states populated in all or substantially all subspaces.

The true ground state (or in some cases, another state) of the spin ensemble can be reached by coupling between the spin-J subspaces. This may be achieved by an interaction that breaks the global SU(2) symmetry of the system Hamiltonian, for example, as described with respect to FIG. 1C. In some examples, the secular dipole-dipole interaction between spins, T2 relaxation, an external gradient field, or a similar external or internal dephasing interaction is sufficient to break this symmetry.

In some implementations, applying the cooling algorithm in the presence of a perturbation that breaks this symmetry allows cooling to the true ground state. In the case of the dipole-dipole interaction, simulations suggest that the spins can be cooled to the true ground state at a factor of approximately $\sqrt{N_s}/2$ times the cooling rate of the Dicke subspace. This gives an effective relaxation time to the true ground state of $$T_{1,dipole} = \frac{1}{\Gamma_s \sqrt{N_s}}.$$

As in the other examples above, we consider a model that includes an exponential rate ($1/T_{1,dipole}$) that is analogous to the thermal spin-lattice relaxation rate ($1/T_1$).

FIG. 7 is a plot 700 showing effective cooling times calculated for example spin ensembles. The plot 700 includes a log-scaled vertical axis 702 showing a range of cooling times in units of seconds, and a log-scaled horizontal axis 704 showing a range of values for the number of spins in the spin ensemble $N_s$. Three curves are shown in the plot 700. The curve 708 represents the cooling times for example spin ensembles under the thermal $T_1$ relaxation process. The other two curves represent the cooling times for the same example spin ensembles under the non-thermal, coherent, cavity-based cooling processes described above. In particular, the curve 706a represents the effective cooling times for a spin ensemble to reach the true ground state, and the curve 706b represents the effective cooling times for the Dicke subspace to reach its ground state.

FIG. 7 was generated based on a model of an electron spin ensemble in an X-band ESR system. In the model used for these calculations, the resonator and spin ensemble are both cooled to liquid helium temperatures (4.2 K). A typical thermal $T_1$ at this temperature is three seconds for a sample of irradiated quartz. The thermal $T_1$ is independent of the number of spins in the sample, as shown by the curve 706a in FIG. 7.

To obtain the curve 706b in FIG. 7, showing the effective cooling time constant for the Dicke subspace of a sample subjected to cavity-based cooling, we solved a Markovian master equation for a spin system having a spin-resonance frequency of 10 GHz. The model used for the calculations included a cavity-spin coupling of 1 Hz, a cavity dissipation rate of 1 MHz, a cavity detuning outside the bandwidth of the resonator, and a Rabi drive strength equal to this detuning. To obtain the curve 706a in FIG. 7, showing the effective cooling time constant for the full spin ensemble under cavity-based cooling with dipolar interaction, we based our results on small numbers of spins and extrapolated to larger numbers. Our initial findings suggest that $$T_{1,eff} \approx \sqrt{N_s} T_{1,Dicke}.$$

As noted above, we consider a spin polarization model that evolves according to an exponential rate ($1/T_{1,eff}$), which is analogous to the thermal spin-lattice relaxation process, which evolves according to an exponential rate ($1/T_1$).

For the examples shown in FIG. 7, if the sample is initially restricted to the Dicke subspace, cavity-based cooling gives a speed up over thermal $T_1$ for samples of greater than $10^5$ spins. If we consider a completely mixed sample, by including a dipolar interaction while performing cavity-based cooling of the spin ensemble, we obtain a speed up over thermal $T_1$ for samples of greater than $10^{10}$ spins.

In the model for cavity-based cooling of a spin ensemble presented above, several assumptions are made for illustration purposes. In some instances, the results and advantages described above can be achieved in systems that do not adhere to one or more of these assumptions. First, we have assumed that the spin ensemble is magnetically dilute such that no coupling exists between spins. A spin-spin interaction that breaks the global SU(2) symmetry of the Tavis-Cummings (TC) Hamiltonian will connect the spin-J subspaces in the coupled angular momentum decomposition of the state space. Such an interaction may be used as an additional resource that should permit complete polarization of the full ensemble Hilbert space. Second, we have neglected the effects of thermal relaxation of the spin system. In some instances, as the cooling effect of the cavity on the spin system relies on a coherent spin-cavity information exchange, the relaxation time of the spin system in the frame of the Rabi drive—commonly referred to as $T_{1,\rho}$—should be significantly longer than the inverse cavity dissipation rate $1/\kappa$. Third, we have assumed that the spin-cavity coupling and Rabi drive are spatially homogeneous across the spin ensemble. Inhomogeneities may be compensated for, for example, by numerically optimizing a control pulse that implements an effective spin-locking Rabi drive of constant strength over a range of spin-cavity coupling and control field amplitudes.

In some implementations, the ability of the cavity to remove energy from the spin system depends at least partially on the cooling power of the cooling system used to cool the cavity. In the example simulations presented above, the cooling power of the cooling system is taken to be infinite, corresponding to an infinite heat capacity of the cavity. The techniques described here can be implemented in a system where the cavity has a finite heat capacity. In FIGS. 8A and 8B, we give a model of the flow of entropy and energy in an example cavity-based cooling process.

FIG. 8A is a schematic diagram 800 showing entropy flow in an example cavity-based cooling process. In the diagram 800, the spins 802 represent a spin ensemble, the cavity 804 represents a cavity that is coupled to the spin ensemble, for example, under the conditions described above, and the fridge 806 represents a refrigerator or another type of cooling system that cools the cavity. Energy removed from the spin ensemble flows to the cavity at a rate of $\Gamma_{SC}$, and energy is removed from the cavity at a rate of $\Gamma_{CF}$ by the (finite) cooling power of the refrigerator.

FIG. 8B is a plot 810 showing example values of the dissipation rates $\Gamma_{SC}$ and $\Gamma_{CF}$. The plot 810 includes a vertical axis 812 representing a range of values for cooling power in units of microwatts (μW), and a log-scaled horizontal axis 814 showing a range of values for the number of spins in the spin ensemble N. Because the cooling power of the fridge 806 is held constant in the simulations represented in the plot 810, the rate $\Gamma_{CF}$ of entropy removal from the cavity to the refrigerator remains constant, as shown by the curve 816a. The rate $\Gamma_{SC}$ of entropy removal from the spin ensemble to the cavity, represented by the curve 816b, was calculated by specifying the total energy to be removed from the spin system to polarize it divided by the time over which that energy is removed, calculated based on our derived cooling times. The total energy removed from the spin system was calculated as $(N_s/2)\hbar\omega$, where ω was taken to be 2π10 GHz. In the examples shown, the spin system is an electron spin ensemble that starts in the fully mixed state such that half the spins must be driven to their ground state.

Energy deposited into the cavity is removed by the fridge at a rate that is based on the cooling power of the fridge, which is typically on the order of tens of microwatts (as shown in FIG. 8B) in some example applications. The curve 816b in FIG. 8B demonstrates that under some conditions, for ensembles larger than roughly $10^{13}$ electron spins, a bottleneck of entropy flow may exist that will limit the minimum cooling time for larger ensembles. However, in the example shown, an ensemble of $10^{12}$ electron spins may be cooled in roughly 3.18 microseconds (μs) given a fridge with cooling power of 50 μW. An ensemble of this size is sufficient to obtain a strong electron spin resonance signal.

Finally, the derivation of the Markovian master equation above assumes that no correlations between cavity and spin system accrue during the cooling process, such that there is no back action of the cavity dynamics on the spin system. This condition is enforced when the cavity dissipation rate, κ, exceeds the rate of coherent spin-cavity exchange in the lowest excitation manifold by at least an order of magnitude (i.e. $\kappa \geq 10\, g\sqrt{N_s}$). In this Markovian limit, the rate at which spin photons are added to the cavity is significantly less than the rate at which thermal photons are added, meaning the cooling power of the fridge necessary to maintain the thermal cavity temperature is sufficient to dissipate the spin photons without raising the average occupation number of the cavity. From the above equation we see that the cooling efficiency could be improved by adding more spins to make κ closer to $g\sqrt{N_s}$; in this regime the cooling power of the fridge may not be sufficient to prevent back action from the cavity and non-Markovian effects significantly lower the cooling rate.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable subcombination.

Example implementations of several independent, general concepts have been described. In one general aspect of what is described above, a drive field is applied to a spin ensemble in a static magnetic field. The drive field is adapted to couple spin states of the spin ensemble with one or more cavity modes of a cavity. Polarization of the spin ensemble is increased by the coupling between the spin states and the cavity mode.

In another general aspect of what is described above, a cavity is coupled with a spin ensemble in a sample. The sample can be held at a thermal temperature and subject to a static magnetic field, and an interaction between the cavity and the spin ensemble is generated (e.g., by applying a drive field). The interaction increases polarization of the spin ensemble faster than the internal polarizing process affecting the sample.

In some implementations of the general concepts described above, polarization of the spin ensemble is increased by cavity-based cooling acting independently on each angular momentum subspace of the spin ensemble via the coupling between the spin states and the cavity mode, and a mixing process mixing the angular momentum subspaces. The operations can be applied iteratively in some instances. The angular momentum subspaces can be mixed, for example, by a dipolar interaction, a transverse ($T_2$) relaxation process, application of a gradient field, or a combination of these and other processes.

In some implementations of the general concepts described above, the cavity has a low mode volume and a high quality factor. The mode volume, the quality factor, or a combination of these and other cavity parameters can be designed to produce a coupling between the spin ensemble and the cavity that effectively "short-circuits" the spin ensemble polarization process. In some examples, the cavity has a mode volume V and a quality factor Q, such that $\kappa \gg g\sqrt{N_s}$. Here, $N_s$ represents the number of spins in the spin ensemble, $\kappa = (\omega_c/Q)$ represents the dissipation rate of the cavity, $\omega_c$ represents the resonance frequency of the cavity, and g represents the coupling strength of the cavity to an individual spin in the spin ensemble. In some examples, the dissipation rate κ is more than two times $g\sqrt{N_s}$. In some examples, the dissipation rate κ is an order of magnitude greater than $g\sqrt{N_s}$. In some examples, the dissipation rate κ is two or three orders of magnitude greater than $g\sqrt{N_s}$. In some instances, the coupling between the spin ensemble and the cavity increases polarization of the spin ensemble faster than the thermal spin-lattice ($T_1$) relaxation process.

In some implementations of the general concepts described above, the spin ensemble has a spin-resonance frequency ($\omega_s$), and the drive field is generated by a resonator that is on-resonance with the spin-resonance frequency ($\omega_s$). The drive field can be a time-varying (e.g., oscillating or otherwise time-varying) magnetic field. In some cases, the spin ensemble is a nuclear spin ensemble, and the drive field is a radio-frequency field. In some cases, the spin ensemble is an electron spin ensemble, and the drive field is a microwave-frequency field.

In some implementations of the general concepts described above, the cavity mode corresponds to a cavity-resonance frequency ($\omega_c$), and the cavity-resonance frequency ($\omega_c$) is detuned from the spin-resonance frequency ($\omega_s$) by an amount $\delta\omega = \omega_c - \omega_s$.

The drive field can have a drive field strength that generates Rabi oscillations at a Rabi frequency ($\Omega_R$). In some cases, the detuning $\delta\omega$ is substantially equal to $\Omega_R$. For instance, the difference $\Delta = \delta\omega - \Omega_R$ can be small compared to the detuning $\Omega\omega$. In some examples, the difference $\Delta$ is less than half the detuning $\delta\omega$. In some examples, the difference $\Delta$ is an order of magnitude less than the detuning $\delta\omega$. In some examples, the difference $\Delta$ is two or three orders of magnitude less than the detuning $\delta\omega$.

In some implementations of the general concepts described above, the interaction between the cavity and the spin ensemble increases polarization of the spin ensemble at a polarization rate that is related to a parameter of the cavity. In some instances, the polarization rate can be higher or lower due to an electromagnetic property of the cavity, such as the value of the quality factor, the value of the mode volume, the value of the dissipation rate, or another property. In some cases, the polarization rate is related to a coupling strength g between the cavity and a spin in the spin ensemble. As an example, the polarization rate can be related to the dissipation rate $$\Gamma_s = \frac{g^2 \kappa}{\kappa^2 + 4\Delta^2},$$

where $\kappa$ represents a dissipation rate of the cavity, g represents the coupling strength of the cavity to a spin in the spin ensemble, and $\Delta = \delta\omega - \Omega_R$. In some cases, the polarization rate is also related to the number of spins in the spin ensemble $N_s$.

In some implementations of the general concepts described above, the static magnetic field is applied to the spin ensemble by a primary magnet system, and the static magnetic field is substantially uniform over the spin ensemble. The drive field can be oriented orthogonal to the static magnetic field. For example, the static magnetic field can be oriented along a z-axis, and the drive field can be oriented in the xy-plane (which is orthogonal to the z-axis).

In some implementations of the general concepts described above, heat energy is removed from the cavity by operation of a cooling system that resides in thermal contact with the cavity. The cooling system can cool the cavity. In some cases, the spin ensemble dissipates photons to the cooling system, or to another thermal environment of the cavity, through the coupling between the spin states and the cavity mode.

In some implementations of the general concepts described above, the drive field is generated by a resonator. In some cases, the resonator and cavity are formed as a common structure or subsystem. For example, the resonator and cavity can be integrated in a common, multi-mode resonator structure. In some cases, the resonator and cavity are formed as two or more separate structures. For example, the resonator can be a coil structure having a first resonance frequency, and the cavity can be a distinct cavity structure that has a second, different resonance frequency. The resonator, the cavity, or both can include superconducting material and other materials.

In some implementations of the general concepts described above, the coupling between the spin ensemble and the cavity changes the state of the spin ensemble. For example, the coupling can map the spin ensemble from an initial (mixed) state to a subsequent state that has higher polarization than the initial state. The subsequent state can be a mixed state or a pure state. In some cases, the subsequent state has a purity that is equal to the purity of the cavity. In some instances, the coupling can evolve the spin ensemble from an initial state to the thermal equilibrium state of the spin ensemble. The thermal equilibrium state is typically defined, at least partially, by the sample environment (including the sample temperature and the static magnetic field strength). In some instances, the coupling can evolve the spin ensemble from an initial state to a subsequent state having a polarization that is less than, equal to, or greater than the thermal equilibrium polarization.

In some implementations of the general concepts described above, the drive field is adapted to couple the Dicke subspace of the spin ensemble with the cavity modes. In some representations of the spin ensemble, the Dicke subspace can be defined as the largest angular momentum subspace, such that the Dicke subspace contains all the totally-symmetric states of the spin ensemble. In some representations, the Dicke subspace corresponds to a system with total angular momentum $J = N_s/2$, where $N_s$ is the number of spins in the spin ensemble. In some cases, the Dicke subspace and multiple other angular momentum subspaces of the spin ensemble are coupled with the cavity modes. In some cases, all angular momentum subspaces of the spin ensemble are coupled with the cavity modes.

In some implementations of the general concepts described above, the interaction between the cavity and the spin ensemble causes the spin ensemble to dissipate photons to a thermal environment via the cavity modes. The interaction can include a coherent radiative interaction between the cavity and the spin ensemble. In some cases, the coherent radiative interaction can increase the spin ensemble's polarization faster than any incoherent thermal process (e.g., thermal spin-lattice relaxation, spontaneous emission, etc.) affecting the spin ensemble. In some cases, the interaction drives the spin ensemble so that it interacts collectively with the cavity as a single dipole moment.

A number of embodiments have been described. Nevertheless, it will be understood that various modifications can be made. Accordingly, other embodiments are within the scope of the following claims.

The invention claimed is:
1. A magnetic resonance method comprising:
applying a drive field to a spin ensemble in a static magnetic field, the spin ensemble defining a state space comprising a plurality of angular momentum subspaces, the drive field adapted to couple spin states of the spin ensemble with a cavity mode of a cavity, wherein the cavity mode corresponds to a cavity-resonance frequency ($\omega_c$), the cavity-resonance frequency ($\omega_c$) is detuned from a spin-resonance frequency ($\omega_s$) of the spin ensemble by a detuning $\delta\omega=\omega_c-\omega_s$, the drive field generates Rabi oscillations at a Rabi frequency ($\Omega_R$), and the difference between the detuning ($\delta\omega$) and the Rabi frequency ($\Omega_R$) is small compared to the detuning ($\delta\omega$); and increasing polarization of the spin ensemble by the coupling between the spin states and the cavity mode acting independently on each of the plurality of angular momentum subspaces of the spin ensemble.

2. The method of claim 1, comprising increasing polarization of the spin ensemble by iteratively:

acting on the angular momentum subspaces of the spin ensemble by the coupling between the spin states and the cavity mode; and mixing the angular momentum subspaces.

3. The method of claim 2, where the angular momentum subspaces are mixed by at least one of a dipolar interaction, a transverse ($T_2$) relaxation process, or application of a gradient field.

4. The method of claim 2, comprising increasing polarization of the spin ensemble faster than a thermal ($T_1$) relaxation process of the spin ensemble.

5. The method of claim 1, wherein the drive field is generated at the spin-resonance frequency ($\omega_s$).

6. The method of claim 1, wherein the spin ensemble comprises nuclear spins, and the drive field is generated at a radio frequency that is related to a gyromagnetic ratio of the nuclear spins and a field strength of the static magnetic field.

7. The method of claim 1, wherein the spin ensemble comprises electron spins, and the drive field is generated at a microwave frequency that is related to a gyromagnetic ratio of the electron spins and a field strength of the static magnetic field.

8. The method of claim 1, wherein the coupling between the cavity mode and the spin states cools the spin ensemble.

9. The method of claim 1, wherein the coupling between the cavity mode and the spin states heats the spin ensemble.

10. The method of claim 1, further comprising removing heat energy from the cavity by operation of a cooling system in thermal contact with the cavity.

11. The method of claim 1, wherein the drive field is oriented orthogonal to the static magnetic field.

12. A magnetic resonance system comprising:

a resonator configured to apply a drive field to a spin ensemble in a static magnetic field, the spin ensemble defining a state space comprising a plurality of angular momentum subspaces, the drive field adapted to couple spin states of the spin ensemble with a cavity mode of a cavity, wherein the cavity mode corresponds to a cavity-resonance frequency ($\omega_c$), the cavity-resonance frequency ($\omega_c$) is detuned from a spin-resonance frequency ($\omega_s$) of the spin ensemble by a detuning $\delta\omega=\omega_c-\omega_s$, the drive field generates Rabi oscillations at a Rabi frequency ($\Omega_R$), and the difference between the detuning ($\delta\omega$) and the Rabi frequency ($\Omega_R$) is small compared to the detuning ($\delta\omega$); and the cavity configured to increase polarization of the spin ensemble by the coupling between the spin states and the cavity mode of the cavity acting independently on each of the plurality of angular momentum subspaces of the spin ensemble.

13. The system of claim 12, wherein the resonator and the cavity are distinct structures.

14. The system of claim 12, comprising an integrated multi-mode resonator structure that includes the resonator and the cavity.

15. The system of claim 12, further comprising:

a primary magnet system adapted to generate the static magnetic field; and a sample containing the spin ensemble.

16. The system of claim 12, further comprising a cooling system thermally coupled to the cavity and adapted to cool the cavity.

17. The system of claim 16, wherein the cooling system comprises at least one of a liquid nitrogen cryostat, a liquid helium cryostat, a closed-loop refrigerator, a pumped-helium cryostat, a helium-3 refrigerator, or a dilution refrigerator.

18. The system of claim 16, wherein the cooling system is thermally coupled to a sample containing the spin ensemble, and adapted to cool the sample.

* * * * *

UNITED STATES PATENT AND TRADEMARK OFFICE
CERTIFICATE OF CORRECTION

PATENT NO. : 10,197,641 B2  
APPLICATION NO. : 14/787575  
DATED : February 5, 2019  
INVENTOR(S) : Troy Borneman, David G. Cory and Christopher James Wood Page 1 of 2

It is certified that error appears in the above-identified patent and that said Letters Patent is hereby corrected as shown below:

In the Specification

Column 2, Detailed Description, Line 51, Delete "(1/T$_{1,eff}$)" and insert --(1/T$_{1, eff}$)-- therefor Column 5, Detailed Description, Line 25, Delete "$\sqrt{N_s}$(the" and insert --$\sqrt{N_s}$ (the -- therefor Column 6, Detailed Description, Line 57, Delete "spin-1/2particles." and insert --spin-1/2 particles.-- therefor Column 7, Detailed Description, Line 5, Delete "spin-1/2Particle," and insert --spin-1/2 particle,-- therefor Column 7, Detailed Description, Line 12, Delete "eignevalues" and insert --eigenvalues-- therefor Column 7, Detailed Description, Line 28, Delete "$Z=\Sigma e^{-H/kT}$ where" and insert --$Z=\Sigma e^{-H/kT}$, where-- therefor Column 7, Detailed Description, Line 43, Delete "$J_z \equiv \Sigma_{j=1}^{N_s} \sigma_z^{(j)}/2$" and insert --$J_z \equiv \sum_{j=1}^{N_s} \sigma_z^{(j)}/2$-- therefor Column 9, Detailed Description, Line 21, Delete "A$_k$ (t)" and insert --A$_k$(t)-- therefor Column 9, Detailed Description, Lines 26-27, Delete "$E_k = i\omega_k(A_k e^{-i\omega_k t+ik.r} - A^*_k e^{i\omega_k t-ik.r})$," and insert --$E_k = i\omega_k\left(A_k e^{-i\omega_k t+ik.r} - A^*_k e^{i\omega_k t-ik.r}\right)$,-- therefor Column 9, Detailed Description, Lines 28-29, Delete "$B_k = ik \times (A_k e^{-i\omega_k t+ik.r} - A^*_k e^{i\omega_k t-ik.r})$," and insert --$B_k = ik \times \left(A_k e^{-i\omega_k t+ik.r} - A^*_k e^{i\omega_k t-ik.r}\right)$,-- therefor Column 10, Detailed Description, Line 10, Delete "$H=\hbar\omega(a^+a+½)$." and insert --$H = \hbar\omega\left(a^+a + \frac{1}{2}\right)$.-- therefor Signed and Sealed this  
Thirtieth Day of July, 2019

Andrei Iancu  
*Director of the United States Patent and Trademark Office*

CERTIFICATE OF CORRECTION (continued)

Column 10, Detailed Description, Lines 27-28, Delete "$\alpha^+\alpha|n\rangle_c = n|n\rangle_c$" and insert --$a^\dagger a|n\rangle_c = n|n\rangle_c$-- therefor Column 10, Detailed Description, Line 54, Delete "u (r, t)" and insert --u(r, t)-- therefor Column 12, Detailed Description, Line 39, Delete "spin-1/2particles" and insert --spin-1/2 particles-- therefor Column 13, Detailed Description, Line 24, Delete ",J-1,J ," and insert --,J-1,J,-- therefor Column 13, Detailed Description, Lines 36-37, Delete "$H^{(1)}=\delta\omega a^\dagger a+\Omega_R J_x+g(a^\dagger J_- +aJ_+).$" and insert --$\tilde{H}^{(1)} = \delta\omega a^\dagger a + \Omega_R J_x + g(a^\dagger J_- + aJ_+).$-- therefor Column 13, Detailed Description, Line 38, Delete "$\delta\omega=\omega_c\omega_s$" and insert --$\delta\omega=\omega_c\omega_s$-- therefor Column 14, Detailed Description, Line 3, Delete "$(\delta\omega, \Omega_R \gg 1/t_c.$" and insert --$(\delta\omega, \Omega_R \gg 1/t_c).$-- therefor Column 15, Detailed Description, Line 53, Delete "$\Omega_s$is" and insert --$\Omega_s$ is-- therefor Column 17, Detailed Description, Lines 4-5, Delete "$\vec{P}_{J_j}(t)=\exp(t\Gamma_s M_j)\vec{P}_j(0)$" and insert --$\vec{P}_{I_j}(t) = \exp(t\Gamma_s M_j)\vec{P}_j(0)$-- therefor Column 17, Detailed Description, Line 37, Delete "$\langle J_,(t)\rangle$" and insert --$\langle J_x(t)\rangle$-- therefor Column 17, Detailed Description, Line 46, Delete "$T_{1, eff}=\lambda(2J)^\gamma/\Gamma_s.$" and insert --$T_{1, \text{eff}} = \lambda(2J)^\gamma/\Gamma_s$-- therefor Column 19, Detailed Description, Line 7, Delete "⊗2" and insert --⊗3-- therefor Column 19, Detailed Description, Line 18, Delete "spin-1/2subspaces" and insert --spin-1/2 subspaces-- therefor Column 19, Detailed Description, Line 27, Delete "spin-3/2subspace" and insert --spin-3/2 subspace-- therefor Column 19, Detailed Description, Line 51, Delete "T2" and insert --$T_2$-- therefor Column 19, Detailed Description, Lines 63-66, After "$T_{1,\text{dipole}} = \frac{1}{\Gamma_s\sqrt{N_s}}$", insert --.--

Column 20, Detailed Description, Line 60, Delete "SU (2)" and insert --SU(2)-- therefor Column 21, Detailed Description, Line 37, Delete "N." and insert --$N_s$.-- therefor Column 23, Detailed Description, Line 19, After "$\delta\omega=\omega_c\omega_s$.", delete "¶"

Column 23, Detailed Description, Line 22, Delete "$\delta\omega$is" and insert --$\delta\omega$ is-- therefor Column 23, Detailed Description, Line 24, Delete "$\Omega\omega$." and insert --$\delta\omega$.-- therefor